United States Patent
Ruvkun et al.

(10) Patent No.: US 7,094,889 B2
(45) Date of Patent: *Aug. 22, 2006

(54) AGE-1 POLYPEPTIDES AND RELATED MOLECULES AND METHODS

(75) Inventors: Gary Ruvkun, Newton, MA (US); Jason Morris, New York, NY (US); Heidi Tissenbaum, Belmont, MA (US)

(73) Assignee: The General Hospital Corporation, Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 326 days.

(21) Appl. No.: 08/908,453

(22) Filed: Aug. 7, 1997

(65) Prior Publication Data

US 2001/0016332 A1    Aug. 23, 2001

Related U.S. Application Data

(60) Provisional application No. 60/023,382, filed on Aug. 7, 1996.

(51) Int. Cl.

| | |
|---|---|
| C07H 21/04 | (2006.01) |
| C12N 9/12 | (2006.01) |
| C12N 15/00 | (2006.01) |
| C12N 15/09 | (2006.01) |
| C12N 15/63 | (2006.01) |
| C12N 15/70 | (2006.01) |
| C12N 15/74 | (2006.01) |
| C12N 5/00 | (2006.01) |
| C12N 5/02 | (2006.01) |
| C12Q 1/68 | (2006.01) |
| G01N 33/53 | (2006.01) |

(52) U.S. Cl. ............... 536/23.5; 435/194; 435/320.1; 435/325; 435/6; 435/7.1; 435/70.1

(58) Field of Classification Search ............... 800/8, 800/3, 21, 2; 435/320.1, 325, 375, 194, 6, 435/7.1, 70.1; 424/9.1; 536/23.5
See application file for complete search history.

(56) References Cited

FOREIGN PATENT DOCUMENTS

WO    US97/13914    9/1997

OTHER PUBLICATIONS

Genbank accession No. Q04441. JO2096597A , 1990.*
Leung TK et al. 1990. Genbank accession No. p. 17066.*
Miyazaki K et al. 1992. Genbank accession No. p. 33197.*
Clements JE et al. Clinical Microbiology Reviews 9:100-117, 1996.*
Hiles et al 1992. Genbank accession No. A43322.*
Goode et al 1994. Genbank accession No. R46294.*
Wilson et al 1994. Genbank accession No. Z66519.*
J Rudinger, Peptide Hormones, "Characteristics of the amino acids as components of a peptide hormone sequence," Jun. 1976, pp. 1-7.*
Friedman et al., "A Mutation in the age-1 Gene in *Caenorhabditis elegans* Lengthens Life and Reduces Hermaphrodite Fertility", *Genetics*, 118: 75-86, (1988).
Hodes et al., "Longevity Assurance Genes: How Do They Influence Aging and Life Span?", *JAGS*, 44: 988-991, (1996).
Johnson et al., "Comparing mutants, selective breeding, and transgenics in the dissection of aging processes of *Caenorhabditis elegans*", *Genetica*, 91: 65-77, (1993).
Lithgow et al., "Molecular genetics of *Caenorhabditis elegans* life span", *Journal of Cell. Biochem. Suppl.*, 17:144, (1993).
Murakami et al., "A Genetic Pathway Conferring Life Extension and Resistance to UV Stress in *Caenorhabditis elegans*", *Genetics*, 143: 1207-1218, (1996).
Hu et al., "Cloning of a novel ubiquitously expressed human phosphatidylinositol", *Database Online*, Accession No. P42338,(1995).
Swinburne, "The *C. elegans* Sequencing Consortium", *Database Online*, Accession No. Z66519, (1995).
Whitman et al., "Type I phosphatidylinositol kinase makes a novel inositol phospholipid, phosphatidylinositol-3-phosphate", *Nature*, 332: 644-646, (1988).
Bernard, V. et al..,*Experientia*, vol. 52, p. A37, abstract S10-47, The *C. elegans* phosphatidylinositol 3-kinase (VPS34).
Tedesco, P.M. et al., 'Cloning a gene for life-extension in *Caenorhabditis elegans*,' abstract, UCLA Symposium on Molecular and Cellular Biology, New Series, 1990, vol. 123, pp. 3-17, database CAPLUS on STN, Institute of Behavioral Genetics, (Boulder, Colorado, USA).
Morris, J.Z. et al., *Nature*, Aug. 1996, vol. 382, pp. 536-539, A phosphtidylinositol-3-OH kinase family member regulating longevity and diapause in *Caenorhabditis elegans*.
Malone, E.A. et al., *Genetics*, Jul. 1996, vol. 143, No. 3, pp. 1193-1205, Genetic analysis of the roles of daf-28 and age-1 in regulating *Caenorhabditis elegans* dauer formation.
Alberts et al., Molecular Biology of the Cell, Second Edition. New York: Garland Publishing, Inc., pp. 258-266, 1989.
Dorman, J.B. et al., *Genetic*, 141(4), 1399-1406 (1995).
Gottlieb, S. et al., *Genetics*, 137, pp. 107-120 (1994), daf-2, daf-16 and daf -23: Genetically Interacting Genes Controlling Dauer Formation In *Caenorhabditis elegans*.
Jazwinski, s. Michal, *Science*, vol. 273, pp. 54-59 (1996), Longevity, Genes, and Aging.
Kenyon, C. et al., *Nature*, 366, pp. 461-464 (1993).
Kenyon, C., *Cell*, 1996, 84(4): pp. 501-504 (1996).
Kimura, K.D. et al., *Science*, 277(5328): pp. 942-946 (1997).
Larsen, P.L. et al., *Genetics*, 139, pp. 1567-1583 (1995).
Larsen, P., *Proc. Natl. Acad. Sci.*, 90, pp. 8905-8909 (1993).
Lin, K. et al., *Science*, 278(5341): pp. 1319-1322 (1997).
Ogg, S. et al., *Nature*, 389(6654): pp. 994-999 (1997).
Okada, T. et al., *J. Biol. Chem.*, 269, pp. 3563-3567 (1994).
Thelen, M. et al., *Proc. Natl. Acad.*, Sci. 91, pp. 4950-4964 (1994).
VanFleteren, J.R., *J. Biochem.*, 292, pp. 605-608 (1993.
Vowels, J.J. et al., *Genetics*, 130, pp. 105-123 (1992).

* cited by examiner

*Primary Examiner*—Peter Paras, Jr.
(74) *Attorney, Agent, or Firm*—Clark & Elbing LLP

(57) ABSTRACT

Disclosed are substantially pure AGE-1 polypeptides and purified DNAs, vectors, and cells encoding those polypeptides. Also disclosed are methods for determining longevity and isolating antagonists using the AGE-1 sequence.

9 Claims, 11 Drawing Sheets

Fig. 3-1

```
Age-1    KLKS........................EEFEVGWVNMSLTDWRDELRQGQFLEHLWAPEPTANR....SRIG 515
Alpha    .VKGRKGAK.................EEHCPLAWGNINLFDYTDTLVSGKMAINLW...PVPHGLEDLLNPIG 460
Beta     KVKTKKSTKTINPSKYQTIRKAGKVHYPVAWVNTMVFDFKGQLRTGDIILHSW..SSFPDELEEMLNPMG 477
Gamma    PALSSKASAESPSSESKGKVRL......LYYVNLLEIDHRFLLRGEYVLHMWQISGKGEDQGSFNADKL 501

Age-1    ENGARIGTNAAVTIEI...SSYGGRVRMPS....QGQYTYLVKHRSTWTETLNIMGDDYESCIRDPGYKK 578
Alpha    VTGSNPNKE.TPCLELEF.DWFSSVVKFPDMSVIEEHANWSVSREAGFSYSHTGLSNRLARDNELRENDK 528
Beta     TVQTNPYTENATALHVKFPENKKQPYYYPFFDKIIEKAAEIASSDSANVSSRGG..KKFLP..... 536
Gamma    TSATNPDKENSMSISI.LLDNYCHPIALPKHQPTPDPEGDRV..........RAEMPNQL....... R551
                                                                        *m333

Age-1    LQM.LVKKHESGIVLEEDEQRHVWMWRRYIQKQEPDLIVLSELAFVWTDRENFSELYVMEKW...... K642
Alpha    EQL.RALCTRDPLSEITEQEKDFLWSHRHYCVTI.PEILPKLL.LSVKWNSRDEVAQMYCLIVKDW.. P591
Beta     .VLKEILDRDPLSQLCENEMDLIWTLRQDCREIFPQSLPKLL.LSIKWNKLEDVAQLQALQIW..... P599
Gamma    KQLEAIIATDPLNPLTAEDKELLWHFRYESLK.HPKAYPKLF.SSVKWGQQEIVAKTYQLARREVWDQS 619
                                                                        +mg109

Age-1    PPSVAALTLLGKRCTDRVIRK AVEKLNEQLSPVTFHLELPLIQALKYEPRAQSEVGMLLTRALCDY 712
Alpha    PIKPEQAMELLDCNYPDPMVSFAVRCLEKYLTDDKLSQYLIQLVQVLKYEQYLDNLFVRFLKKALTN Q661
Beta     KLPPREALELLDFNYPDQYVREYAVGCLRQ.MSDEELSQYLLQLVQLVKYEPFLDCALSRFLLERAL GNR668
Gamma    ALDVGLTMQLLDCNFSDENVRAIAVQKLES.LEDDDVLHYLLQLVQAVKFEPYHDSALARFLKRGLR NK688

Age-1    RIGHRLFWLLRAEIARLRDCDLKSEEYRRISLLMEAYLRG.NEEHIKIITRQVDMVDELTRISTLVK GMP781
Alpha    RIGHFFFWHLKSEM.HNKTVSQ......RFGLLLESYCRACG.MYLKHLNRQVEAMEKLINLTDILK ...720
Beta     RIGQFLFWHLRSEV.HIPAVSV......QFGVILEAYCRGSV.GHMKVLSKQVEALNKLKTLNSLIK ...727
Gamma    RIGHFLFWFLRSEIAQSRHYQQ......RFAVILEAYLRGCGTAMLHDFTQQVQIEMLQKVTLDIKS LS752

Age-1    KDVATMK......LRDEER..SISHKMENMDSPLDPVYKLGEMIIDKAIVLGSAKRPLMLHWKNKNP HWKNP840
Alpha    QEKKDETQKV..QMKFLVEQMRQPDFMDALQGFLSPLNPAHQLGNLRLEECRIMSSAKRPLWLNWEN PDI788
Beta     LNAVKLNRAK..GKEAMHTCLKQSAYREALSDLQSPLNPCVILSELYVEKCKYMDSKMKPLWLVYNN KVF795
Gamma    AEKYDVSSQVISQLKQKLENLQNSQLPESFRV...PYDPGLKAGALAIEKCKVMASKKKPLWLEFKC AD.818

Age-1    KSDLHLPFCAMIFKNGDDLRQDMLVLQVEVMDNIWKAANIDCCLNPYAVLPMGEMIGIIEVVPNCKT IF910
Alpha    MSELLFQNNEIIFKNGDDLRQDMLTLQIIRIMENIWQNQGLDLRMLPYGCLSIGDCVGLIEVVRNSH TIM858
Beta     GEDSV...GVIFKNGDDLRQDMLTLQMLRLMDLLWKEAGLDLRMLPYGCLATGDRSGLIEVVSTSET IA861
Gamma    PTALSNETIGILFKHGDDLRQDMLILQILRIMESIWETESLDLCLPYGCISTGDKIGMIEIVKDATT IA888
```

Fig. 3-2

```
           mg55
Age-1  EIQVGTGFMNTAVRSIDPSFMNKWIRKQCGIEDEKKKSKKDSTKNPIEKKIDNTQAMKKYFESVDRFLYS 980
Alpha  QIQ.CKGGLKGAL.QFNSHTHQWLKD..................KNKGEI.YD.....AAIDLFTRS 900
Beta   DIQLNSSNVAAAA.AFNKDALNWLKE..................YNSGDD.LD.....RAIEEFTLS 904
Gamma  KIQ..QSTVGNTG.AEKDEVLNHWLKE..................KSPTEEKFQ......AAVEREVYS 930

Age-1  CVGYISVATYIMGIKDRHSDNLWLTEDGKYVHIDFGHILGHGKTKLGIQRDRQPFILTEHFMTVIRSGKSV 1050
Alpha  CAGYCVATFILGIGDRHNSNIMVKDDGQLFHIDFGHFLDHKKKKFGYKRERVPFVLTQDFLIVISKGAQE 970
Beta   CAGYCVASYVLGIGDRHSDNIMVKKTGQLFHIDFGHILGNFFKSKFGIKRERVPFILTYDFIHVIQQG..K 972
Gamma  CAGYCVATFVLGIGDRHNDNIMITETGNLFHIDFGHILGNYKSFLGINKERVPFVLTDFLFVMGTSGKK 1000
                     mg55

Age-1  DGNSHELQKFKTLCVEAYEVMWNNRDLFVSLFTLMLGMELPELSTKADLDHLKKTLFCNGESKEEARKFF 1120
Alpha  YTKTREFERFQEMCYKAYLAIRQHANLFINLFSMMLGSGMPELQSFDDIAYIRKTL.ALDKTEQEALEYF 1039
Beta   TGNTEKFGRFRQCCEDAYLILRRHGNLFITLFALMLTAGLPELTSVKDIQYLKDSL.ALGKSEEEALKQF 1041
Gamma  TS..PHFQKFQDICVKAYLALRHHTNLLRHTNLFSMMLMTGMPQLTSKEDIEYIRDAL.TVGKNEEDAKKYF 1067

Age-1  AGIYEEAFNGSWSTKTNWLFHAVKHY... 1146
Alpha  TKQMNDAHHGGWTTKMDWIFHTIKQHALN 1068
Beta   KQKFDEALRESWTTKVNWMAHTVRKDYRS 1070
Gamma  LDQIEVWQRQRMDCAV............ 1083
```

Fig. 3-3

(SEQ ID NO:2)

```
   1 cggaagccat ggagctcgag atctgattgc tggacacgga cggaactccg acgtatctcg
  61 cagatgcatg ttaacatttt acatccacaa ctgcaaacga tggtcgagca gtggcaaatg
 121 cgagaacgcc catcgctgga gaccgagaat ggcaaaggat cgctgctcct ggaaaatgaa
 181 ggtgtcgcag atatcatcac tatgtgtcca ttcggagaag ttattagtgt agtatttccg
 241 tggtttcttg caaatgtgcg aacatcgcta gaaatcaagc tatcagattt caaacatcaa
 301 cttttcgaat tgattgctcc gatgaagtgg ggaacatatt ccgtaaagcc acaggattat
 361 gtgttcagac agttgaataa tttcggcgaa attgaagtta tatttaacga cgatcaaccc
 421 ctgtcgaaat tagagctcca cggcactttc ccaatgcttt ttctctacca acctgatgga
 481 ataaacaggg ataaagaatt aatgagtgat ataagtcatt gtctaggata ctcactggat
 541 aaactggaag agagcctcga tgaggaactc cgtcaatttc gtgcttctct ctgggctcgt
 601 acgaagaaaa cgtgcttgac acgtggactt gagggtacca gtcactacgc gttccccgaa
 661 gaacagtact tgtgtgttgg tgaatcgtgc cgaaagatt tggaatcaaa agtcaaggct
 721 gccaagctga gttatcagat gttttggaga aaacgtaaag cggaaatcaa tggagtttgc
 781 gagaaaatga tgaagattca aattgaattc aatccgaacg aaactccgaa atctctgctt
 841 cacacgtttc tctacgaaat gcgaaaattg gatgtatacg ataccgatga tcctgcagat
 901 gaaggatggt tcttcaatt ggctggacgt accacgtttg ttacaaatcc agatgtcaaa
 961 cttacgtctt atgatggtgt ccgttcggaa ctggaaagct atcgatgccc tggattcgtt
1021 gttcgccgac aatcactagt cctcaaagac tattgtcgcc caaaaccact ctacgaacca
1081 cattatgtga gcacacga acgaaaactt gctctagacg tgctcagcgt gtctatagat
1141 agcacaccaa acagagcaa gaacagtgac atggttatga ctgattttcg tccgacagct
1201 tcactcaaac aagtttcact ttgggacctt gacgcgaatc ttatgatacg gcctgtgaat
1261 atttctggat tcgatttccc ggccgacgtg gatatgtacg ttcgaatcga attcagtgta
1321 tatgtgggga cactgacgct ggcatcaaaa tctacaacaa agtgaatgc tcaatttgca
1381 aaatggaata aggaaatgta cacttttgat ctatacatga aggatatgcc accatctgca
1441 gtactcagca ttcgtgtttt gtacggaaaa gtgaaattaa aaagtgaaga attcgaagtt
1501 ggttgggtaa atatgtccct aaccgattgg agagatgaac tacgacaagg acaatttta
1561 ttccatctgt gggctcctga accgactgcc aatcgtagta ggatcggaga aaatggagca
1621 aggataggca ccaacgcagc ggttacaatt gaaatctcaa gttatggtgg tagagttcga
1681 atgccgagtc aaggacaata cacatatctc gtcaagcacc gaagtacttg gacggaaact
1741 ttgaatatta tgggtgatga ctatgagtcg tgtatcagag atccaggata taagaagctt
1801 cagatgcttg tcaagaagca tgaatctgga ttgtattag aggaagatga acaacgtcat
1861 gtctggatgt ggaggagata cattcaaaag caggagcctg atttgctcat tgtgctctcc
1921 gaactcgcat tgtgtggac tgatcgtgag aacttttccg agctctatgt gatgcttgaa
1981 aaatggaaac cgccgagtgt ggcagccgcg ttgactttgc ttggaaaacg ttgcacggat
2041 cgtgtgattc gaaagtttgc agtggagaag ttgaatgagc agctgagccc ggtcacattc
2101 catctttca tattgcctct catacaggcg ttgaagtacg aaccgcgtgc tcaatcggaa
2161 gttggaatga tgctcttgac tagagctctc tgcgattatc gaattggaca tcgactttc
2221 tggctgctcc gtgcagagat tgctcgtttg agagattgtg atctgaaaag tgaagaatat
2281 cgccgtatct cacttctgat ggaagcttac ctccgtggaa atgaagagca catcaagatc
2341 atcacccgac aagttgacat ggttgatgag ctcacacgaa tcagcactct tgtcaaagga
2401 atgccaaaag atgttgctac gatgaaactg cgtgacgagc ttcgatcgat tagtcataaa
2461 atggaaaata tggattctcc actggatcct gtgtacaaac tgggtgaaat gataatcgac
2521 aaagccatcg tcctaggaag tgcaaaacgt ccgttaatgc ttcactggaa gaacaaaaat
2581 ccaaagagtg acctgcacct tccgttctgt gcaatgatct tcaagaatgg agacgatctt
2641 cgccaggaca tgcttgttct tcaagttctc gaagttatgg ataacatctg gaaggctgca
```

Fig. 4-1

```
2701 aacattgatt gctgtttgaa cccgtacgca gttcttccaa tgggagaaat gattggaatt
2761 attgaagttg tgcctaattg taaaacaata ttcgagattc aagttggaac aggattcatg
2821 aatacagcag ttcggagtat tgatccttcg tttatgaata agtggattcg gaaacaatgc
2881 ggaattgaag atgaaaagaa gaaaagcaaa aaggactcta cgaaaaatcc catcgaaaag
2941 aagattgata atactcaagc catgaagaaa tattttgaaa gtgtcgatcg attcctatac
3001 tcgtgtgttg gatattcagt tgccacgtac ataatgggaa tcaaggatcg tcacagtgat
3061 aatctgatgc tcactgaaga tggaaaatat gtccacattg atttcggtca cattttggga
3121 cacggaaaga ccaaacttgg gatccagcga gatcgtcaac cgtttattct aaccgaacac
3181 tttatgacag tgattcgatc gggtaaatct gtggatggaa attcgcatga gctacaaaaa
3241 ttcaaaacgt tatgcgtcga agcctacgaa gtaatgtgga ataatcgaga tttgttcgtt
3301 tccttgttca ccttgatgct cggaatggag ttgcctgagc tgtcgacgaa agcggatttg
3361 gatcatttga agaaaaccct cttctgcaat ggagaaagca agaagaagc gagaaagttt
3421 ttcgctggaa tctacgaaga agccttcaat ggatcatggt ctaccaaaac gaattggctc
3481 ttccacgcag tcaaacacta ctga
```

Fig. 4-2

(SEQ ID NO: 1)

```
   1 MHVNILHPQL QTMVEQWQMR ERPSLETENG KGSLLLENEG VADIITMCPF
  51 GEVISVVFPW FLANVRTSLE IKLSDFKHQL FELIAPMKWG TYSVKPQDYV
 101 FRQLNNFGEI EVIFNDDQPL SKLELHGTFP MLFLYQPDGI NRDKELMSDI
 151 SHCLGYSLDK LEESLDEELR QFRASLWART KKTCLTRGLE GTSHYAFPEE
 201 QYLCVGESCP KDLESKVKAA KLSYQMFWRK RKAEINGVCE KMMKIQIEFN
 251 PNETPKSLLH TFLYEMRKLD VYDTDDPADE GWFLQLAGRT TFVTNPDVKL
 301 TSYDGVRSEL ESYRCPGFVV RRQSLVLKDY CRPKPLYEPH YVRAHERKLA
 351 LDVLSVSIDS TPKQSKNSDM VMTDFRPTAS LKQVSLWDLD ANLMIRPVNI
 401 SGFDFPADVD MYVRIEFSVY VGTLTLASKS TTKVNAQFAK WNKEMYTFDL
 451 YMKDMPPSAV LSIRVLYGKV KLKSEEFEVG WVNMSLTDWR DELRQGQFLF
 501 HLWAPEPTAN RSRIGENGAR IGTNAAVTIE ISSYGGRVRM PSQGQYTYLV
 551 KHRSTWTETL NIMGDDYESC IRDPGYKKLQ MLVKKHESGI VLEEDEQRHV
 601 WMWRRYIQKQ EPDLLIVLSE LAFVWTDREN FSELYVMLEK WKPPSVAAAL
 651 TLLGKRCTDR VIRKFAVEKL NEQLSPVTFH LFILPLIQAL KYEPRAQSEV
 701 GMMLLTRALC DYRIGHRLFW LLRAEIARLR DCDLKSEEYR RISLLMEAYL
 751 RGNEEHIKII TRQVDMVDEL TRISTLVKGM PKDVATMKLR DELRSISHKM
 801 ENMDSPLDPV YKLGEMIIDK AIVLGSAKRP LMLHWKNKNP KSDLHLPFCA
 851 MIFKNGDDLR QDMLVLQVLE VMDNIWKAAN IDCCLNPYAV LPMGEMIGII
 901 EVVPNCKTIF EIQVGTGFMN TAVRSIDPSF MNKWIRKQCG IEDEKKKSKK
 951 DSTKNPIEKK IDNTQAMKKY FESVDRFLYS CVGYSVATYI MGIKDRHSDN
1001 LMLTEDGKYV HIDFGHILGH GKTKLGIQRD RQPFILTEHF MTVIRSGKSV
1051 DGNSHELQKF KTLCVEAYEV MWNNRDLFVS LFTLMLGMEL PELSTKADLD
1101 HLKKTLFCNG ESKEEARKFF AGIYEEAFNG SWSTKTNWLF HAVKHY
```

Fig. 6

AGE-1 POLYPEPTIDES AND RELATED MOLECULES AND METHODS

CROSS REFERENCE TO RELATED APPLICATIONS

This application claims benefit from provisional application No. 60/023,382 filed on Aug. 7, 1996.

BACKGROUND OF THE INVENTION

This invention relates to polypeptides and nucleic acid sequences involved in aging, as well as methods for their use.

As the average age of the population of the United States and other countries increases, there is a growing interest in efforts to delay the aging process. It has long been accepted that environmental factors which trigger DNA damage or are otherwise toxic to cells might negatively influence longevity. Increasingly, the role of genetics in this process has become accepted as well, and has resulted in a search for genes which participate in and control aging or senescence. These genes are valuable because they may encode therapeutic products which retard senescence or death. Alternatively, these proteins may be used as targets for the design or isolation of antagonist-type drugs which themselves prolong life-span or delay the onset of age-related conditions.

SUMMARY OF THE INVENTION

In general, the invention features a substantially pure preparation of AGE-1 polypeptide, the polypeptide having at least 50% (and preferably 70% or 90%) amino acid sequence identity to the polypeptide of FIG. 6 (SEQ ID NO: 1). Preferably, the AGE-1 polypeptide includes identical amino acids in equivalent positions to 50% (and preferably 70% or 90%) of the following amino acids of FIG. 6 (SEQ ID NO: 1): amino acids Gly-32, Leu-73, His-78, Phe-81, Glu-109, Phe-114, Leu-123, Leu-125, Phe-129, Lys-181, Ser-208, Lys-211, Arg-321, Leu-325, Leu-351, Ser-355, Met-373, Leu-381, Leu-393, Thr-432, Tyr-451, Glu-475, Pro-507, Ile-514, Gly-518, Glu-530, Val-538, Leu-582, Tyr-606, Pro-643, Phe-665, Leu-744, Leu-745, Arg-762, Leu-789, Arg-794, Ala-827, Arg-829, Trp-835, Ser-842, Asn-905, Gly-917, Asp-975, Ile-990, Asp-1006, His-1020, Lys-1104, Thr-1105, Gly-1130, Phe-1140, and Lys-1144. An alanine at equivalent amino acid 827 is particularly preferred. In other preferred embodiments, the AGE-1 polypeptide is derived from an animal, for example, *Caenhorabditis elegans* or a mammal, for example, a human.

The invention also features useful fragments of AGE-1 polypeptides; in particular, preferred fragments include amino acids 387–641, 387–1146, 1–130, 1–150, 1–658, or 1–404 of FIG. 6 (SEQ ID NO: 1).

In related aspects, the invention features purified DNA (for example, cDNA) which encodes any of the AGE-1 polypeptides described above or which includes an AGE-1 nucleic acid sequence which is at least 30% (and preferably 40%, 50%, 70%, 80%, or 90%) identical to the nucleic acid sequence of FIG. 4 (SEQ ID NO: 2). In addition, the invention features a purified DNA including an AGE-1 nucleic acid sequence substantially identical to nucleotides 64 to 852 FIG. 4 (SEQ ID NO: 2); a purified DNA including an AGE-1 nucleic acid sequence substantially identical to nucleotides 865 to 912 of FIG. 4 (SEQ ID NO: 2); a purified DNA including an AGE-1 nucleic acid sequence substantially identical to nucleotides 919 to 975 of FIG. 4 (SEQ ID NO: 2); a purified DNA including an AGE-1 nucleic acid sequence substantially identical to nucleotides 1003 to 3090 of FIG. 4 (SEQ ID NO: 2); a purified DNA including an AGE-1 nucleic acid sequence substantially identical to nucleotides 3094 to 3501 of FIG. 4 (SEQ ID NO: 2); and a purified DNA including an AGE-1 nucleic acid sequence substantially identical to nucleotides 2620 to 2655 of FIG. 4 (SEQ ID NO: 2). The invention also features a vector and a cell, each of which includes a purified AGE-1 DNA of the invention; and a method of producing a recombinant AGE-1 polypeptide involving providing a cell transformed with DNA encoding an AGE-1 polypeptide positioned for expression in the cell, culturing the transformed cell under conditions for expressing the DNA, and isolating the recombinant AGE-1 polypeptide. The invention further features recombinant AGE-1 polypeptide produced by such expression of a purified DNA of the invention, and a substantially pure antibody that specifically recognizes and binds an AGE-1 polypeptide.

In addition, the invention features methods of identifying AGE-1 modulatory compounds. The first method involves the identification of a modulatory compound that is capable of decreasing the expression of an AGE-1 gene, involving (a) providing a cell expressing the AGE-1 gene and (b) contacting the cell with a candidate compound, a decrease in AGE-1 expression following contact with the candidate compound identifying a modulatory compound. The second method also involves the identification of a modulatory compound which is capable of decreasing AGE-1 activity (for example, kinase activity); this method involves (a) providing a cell expressing an AGE-1 polypeptide and (b) contacting the cell with a candidate compound, a decrease in AGE-1 activity (for example, kinase activity) following contact with the candidate compound identifying a modulatory compound.

In preferred embodiments of both methods, the AGE-1 gene encodes or AGE-1 polypeptide includes an amino acid sequence that is at least 50% (and preferably 70% or 90%) identical to the amino acid sequence shown in FIG. 6 (SEQ ID NO: 1); and the AGE-1 gene or AGE-1 polypeptide is from an animal (for example, *C. elegans*), and preferably a mammal (for example, a human). In other preferred embodiments, the method is carried out in a nematode or other animal, or the method involves assaying AGE-1 activity in vitro.

The invention further features modulatory compounds identified by the above methods, as well as a method for increasing longevity in a mammal that involves administering such a compound to a mammal (for example, a human).

In addition, the invention features a method of determining the longevity of an animal. The method involves measuring AGE-1 gene expression or AGE-1 activity (for example, kinase activity) in a sample from the animal, with a decrease in AGE-1 expression or activity relative to a wild-type sample being an indication that the animal has increased longevity.

In preferred embodiments, the animal is a mammal (for example, a human); AGE-1 gene expression is measured by assaying the amount of AGE-1 polypeptide in the sample (for example, by immunological methods); or AGE-1 gene expression is measured by assaying the amount of AGE-1 mRNA in the sample (for example, by hybridization or PCR techniques using an AGE-1-specific nucleic acid sequence).

Kits for carrying out the above methods are also included in the invention. Such kits preferably include a substantially pure antibody that specifically recognizes and binds an AGE-1 polypeptide and may also include means for detecting and quantitating antibody binding. Alternatively, the kit may include all or a fragment of an AGE-1 nucleic acid sequence useful for hybridization or PCR purposes and may also include means for detecting and quantitating the products of the hybridization or amplification.

By "AGE-1 polypeptide" is meant a phosphatidylinositol 3-kinase (PI 3-kinase) involved in the control of senescence.

By "protein" or "polypeptide" is meant any chain of amino acids, regardless of length or post-translational modification (e.g., glycosylation or phosphorylation).

By "substantially pure" is meant a preparation which is at least 60% by weight (dry weight) the compound of interest, e.g., the AGE-1 polypeptide or AGE-1-specific antibody. Preferably the preparation is at least 75%, more preferably at least 90%, and most preferably at least 99%, by weight the compound of interest. Purity can be measured by any appropriate method, e.g., column chromatography, polyacrylamide gel electrophoresis, or HPLC analysis.

By "purified DNA" is meant DNA that is not immediately contiguous with both of the coding sequences with which it is immediately contiguous (one on the 5' end and one on the 3' end) in the naturally-occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequence.

By a "substantially identical" nucleic acid is meant a nucleic acid sequence which encodes a polypeptide differing only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the polypeptide (assayed, e.g., as described herein). Preferably, the encoded sequence is at least 30% identical at the amino acid level to the sequence of FIG. 6 (SEQ ID NO: 1) or an AGE-1 domain thereof (as described herein). In other preferred embodiments, the encoded sequence is at least 40%, preferably 50%, more preferably 60%, and most preferably 70% identical at the amino acid level to the sequence of FIG. 6 (SEQ ID NO: 1) or an AGE-1 domain thereof. In still other preferred embodiments, the encoded sequence is at least 80%, preferably 85%, more preferably 90%, and most preferably 95% identical at the amino acid level to the sequence of FIG. 6 (SEQ ID NO: 1) or an AGE-1 domain thereof. If nucleic acid sequences are compared a "substantially identical" nucleic acid sequence is one which is at least 30%, more preferably 40%, and most preferably 50% identical to the sequence of FIG. 4 (SEQ ID NO: 2) or a sequence encoding an AGE-1 domain thereof. In other preferred embodiments, the substantially identical nucleic acid sequence is one which is at least 75%, more preferably 85%, and most preferably 95% identical to the sequence of FIG. 4 (SEQ ID NO: 2) or a sequence encoding an AGE-1 domain. The length of nucleic acid sequence comparison will generally be at least 50 nucleotides, preferably at least 60 nucleotides, more preferably at least 75 nucleotides, and most preferably 110 nucleotides.

Homology is typically measured using sequence analysis software (e.g., Sequence Analysis Software Package of the Genetics Computer Group, University of Wisconsin Biotechnology Center, 1710 University Avenue, Madison, Wis. 53705, BLAST, or PILEUP/PRETTYBOX programs). Such software matches similar sequences by assigning degrees of homology to various substitutions, deletions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By "positioned for expression" is meant that the DNA molecule is positioned adjacent to a DNA sequence which directs transcription and translation of the sequence (i.e., facilitates the production of AGE-1 protein).

By "purified antibody" is meant antibody which is at least 60%, by weight, free from the proteins and naturally-occurring organic molecules with which it is naturally associated. Preferably, the preparation is at least 75%, more preferably at least 90%, and most preferably at least 99%, by weight, antibody.

By "specifically binds" is meant an antibody which recognizes and binds an AGE-1 polypeptide but which does not substantially recognize and bind other molecules in a sample (e.g., a biological sample) which naturally includes AGE-1 polypeptide. An antibody which "specifically binds" AGE-1 is sufficient to detect an AGE-1 protein product in such a biological sample using one or more of the standard immunological techniques available to those in the art (for example, Western blotting or immunoprecipitation).

By "longevity" is meant rate of senescence and/or life-span.

By "relative to a wild-type sample" is meant relative to an equivalent tissue sample from one or more individuals of average life-span. An individual of average life-span may be determined by an analysis of AGE-1 levels in a statistically significant number of members of a population.

By "immunological methods" is meant any assay involving antibody-based detection techniques including, without limitation, Western blotting, immunoprecipitation, and direct and competitive ELISA and RIA techniques.

By "means for detecting" is meant any one or a series of components that sufficiently indicate a detection event of interest. Such means involve at least one label that may be assayed or observed, including, without limitation, radioactive, fluorescent, and chemiluminescent labels.

By "AGE-1 RNA" is meant messenger RNA transcribed from an AGE-1 DNA sequence.

By "hybridization techniques" is meant any detection assay involving specific interactions (based on complementarity) between nucleic acid strands, including DNA-DNA, RNA-RNA, and DNA-RNA interactions. Such hybridization techniques may, if desired, include a PCR amplification step.

By "kinase activity" is meant AGE-1-mediated production of phosphatidylinositol $P_3$ ($PIP_3$).

By a "modulatory compound", as used herein, is meant any compound capable of either decreasing AGE-1 expression (i.e., at the level of transcription, translation, or post-translation) or decreasing AGE-1 protein activity (i.e., the amount of activity, for example, kinase activity, per unit amount of AGE-1 protein).

Other features and advantages of the invention will be apparent from the following detailed description thereof, and from the claims.

Figure 1:
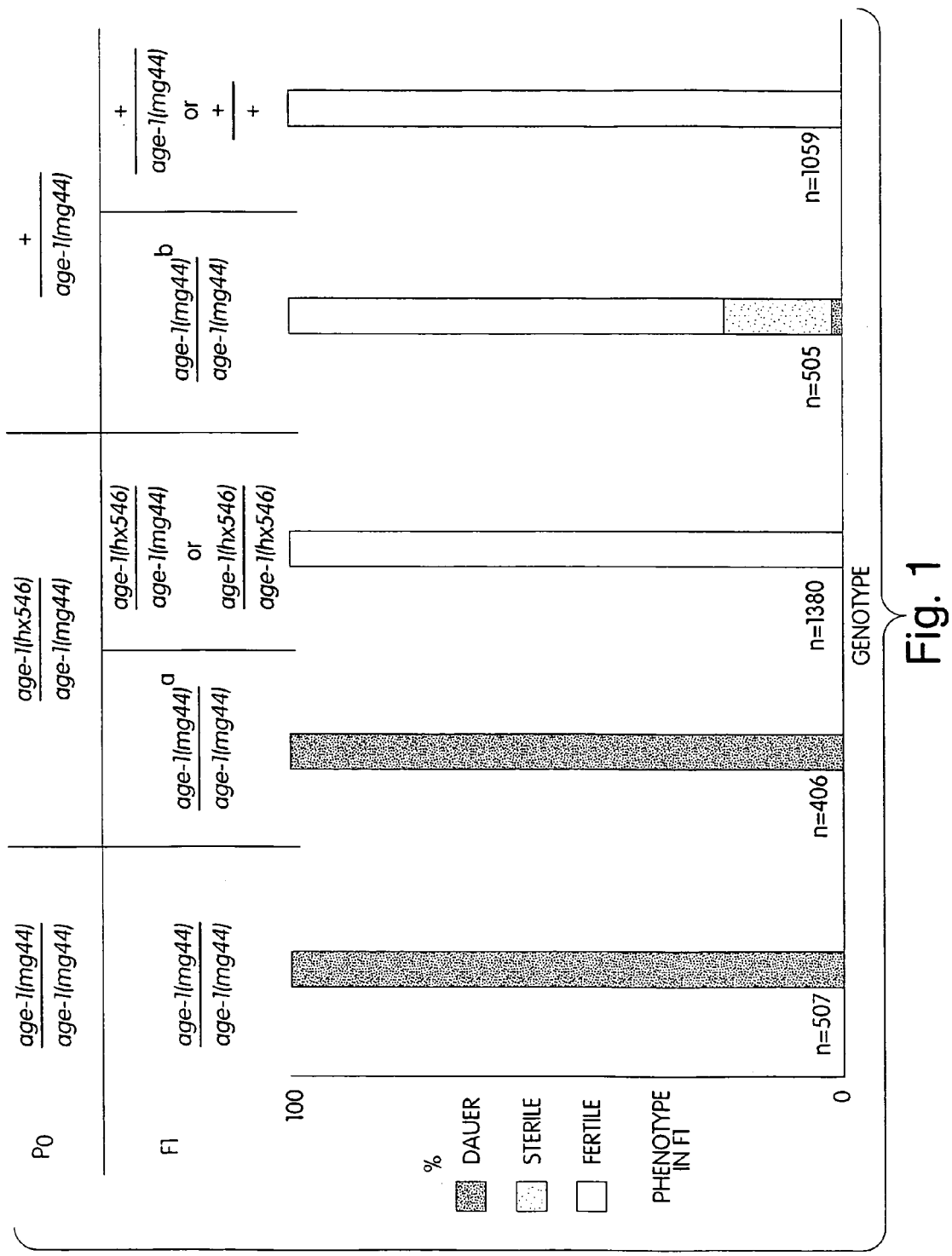
FIG. 1 is a graph showing defective maternal age-1 gene activity in age-1(hx546) animals. The age-1(mg44) chromosome in the figure is marked in cis with sqt-1(sc13). age-1 (mg44) progeny of age-1(mg44) homozygous parents are shown to the left. Progeny of age-1(hx546)/sqt-1(sc13) age-1(mg44) heterozygous parents are shown in the middle. Progeny of +/1sqt-1(sc13) age-1(mg44) heterozygous parents are shown to the right. The sqt-1(sc13) genetic marker was used to identify homozygous age-1(mg44) progeny. Similar results were observed when another marker, unc-4, was used to mark another age-1 allele, m333, that is also likely to be a null allele, and mg109 (data not shown). Animals were grown at 25° C. in the experiment shown. Note that sqt-1(sc13) age-1(mg44) progeny of age-1 (hx546)/sqt-1(sc13) age-1(mg44) arrest development as dauer larvae with 100% penetrance at 25° C. This is the same as control age-1(mg44) daughters of age-1(mg44) parents. In the case of age-1(mg44) daughters of age-1 (mg44) parents, we also noted 6% (n=30) of these animals arrest at the L1 or L2 stage. Many of these arrested animals eventually grow to dauer-like larvae and sterile adults. In contrast, 1% of sqt-1(sc 13) age-1(mg44) progeny of +/sqt-1(sc13) age-1(mg44) arrest development as dauer larvae at 25° C. age-1(hx546)/sqt-1(sc13) age-1(mg44) progeny form fertile adults, just like +/sqt-1(sc13) age-1(mg44) progeny. This shows that age-1(hx546) expresses sufficient zygotic but not maternal levels of age-1 for non-dauer growth.

At 20° C., fewer of the sqt-1(sc13)age-1(mg44) progeny of age-1(hx546)/sqt-1(sc13) age-1(mg44) arrest development as dauer larvae; most continue development as dauer-like animals that are dark and sterile. Such temperature dependent dauer arrest has previously been noted for age-1(mg44) (Gottlieb, S. & Ruvkun, G. *Genetics* 137, 107–120 (1994)). We cannot attribute the more severe phenotype at high temperatures to any temperature sensitivity of age-1 (hx546) because even wild type dauer formation is a temperature dependent process (Golden, J. W. & Riddle, D. L., *Proc. Natl. Acad. Sci.* 81:819–823 (1984)). At 20 degrees, unlike 25 degrees, there is a detectable maternal age-1 activity in age-1(hx546): 4% of sqt-1(sc13) age-1(mg44) progeny of age-1(hx546)/sqt-1(sc13) age-1(mg44) parents are fertile (data not shown), unlike age-1(mg44) daughters of age-1(mg44) mothers (Gottlieb, S. & Ruvkun, G. *Genetics* 137, 107–120 (1994)). In contrast, at 20 degrees, 93% of sqt-1(sc13) age-1(mg44) progeny of +/ sqt-1(sc13) age-1 (mg44) parents are fertile.

In this Figure, superscript [a] indicates that one fertile Sqt adult was a recombinant sqt-1(sc13) age-1(mg44)/sqt-1 (sc13) age-1(hx546). Two other sqt-1(sc13) age-1(mg44)/ sqt-1(sc13) age-1(hx546) recombinants were picked from the same parental strains in other experiments (data not shown). Superscript [b] indicates that all fertile Sqt adults produced all Sqt dauers in the F3 except for three sqt-1(sc13) age-1(mg44)/sqt-1(sc13) recombinants.

The genotype of the recombinants was determined by picking individual animals from the original non-dauer Sqt and then examining its brood. Three sqt-1(sc13) age-1 (hx546)/sqt-1(sc13) age-1(mg44) recombinants map age-1 (hx546) to the right of sqt-1(sc13), because these recombinants show that each time sqt-1(sc13) was recombined away from age-1(mg44) in the age-1(hx546)/sqt-1(sc13) age-1 (mg44) heterozygote, age-1(hx546) was recovered on the sqt-1recombinant chromosome. age-1(hx546) was also three-factor mapped relative to sqt-1(sc13) and lin-29; two Lin non-Sqt recombinants were Age and 10 Sqt non-Lin recombinants were non-Age, based on lack of maternal rescue of age-1(m333). This shows that age-1 maps to the left of lin-29.

To carry out these experiments, age-1(hx546) males were mated into sqt-1(sc13) age-1(mg44) hermaphrodites at 20° C. F1 Non-Sqt Non-Daf cross progeny (3/3) were picked to separate plates. Individual heterozygotes were singled to plates at either 25, 20, or 15 degrees and transferred daily (20° and 25°) or every 2–3 days (20° and 15°). Worms were then counted and scored for dauer and non-dauer either 3 days later (25°), 4 days later (20°), or 7 days later (15°). For genetic mapping, age-1(hx546) males were mated with sqt-1(sc13) lin-29(n333)/mnC1 hermaphrodites, and individual wild type cross progeny were picked to separate plates. Plates that segregated wild type, Sqt Lin animals, and no progeny bearing mnC1 were examined for recombinants that were Sqt-non-Lin and Lin-non-Sqt. Putative recombinants were then picked to individual plates, and progeny from the heterozygous recombinant were singled to establish a homozygous recombinant strain. 10 Sqt-non-Lin and 2 Lin-non-Sqt recombinants were then scored for failure to maternally complement age-1(m333) for dauer constitutivity at 25° C. unc-4(e120) age-1(m333)/mnC1 males were mated with there combinants. The Lin non-Sqt recombinants were opened at the vulva by a microinjection needle prior to mating. Wild-type hermaphrodite cross progeny were singled to 25° C., and their progeny were scored for whether unc-4(e120) age-1(m333) homozygous progeny arrested as dauer larvae.

Figure 2A:
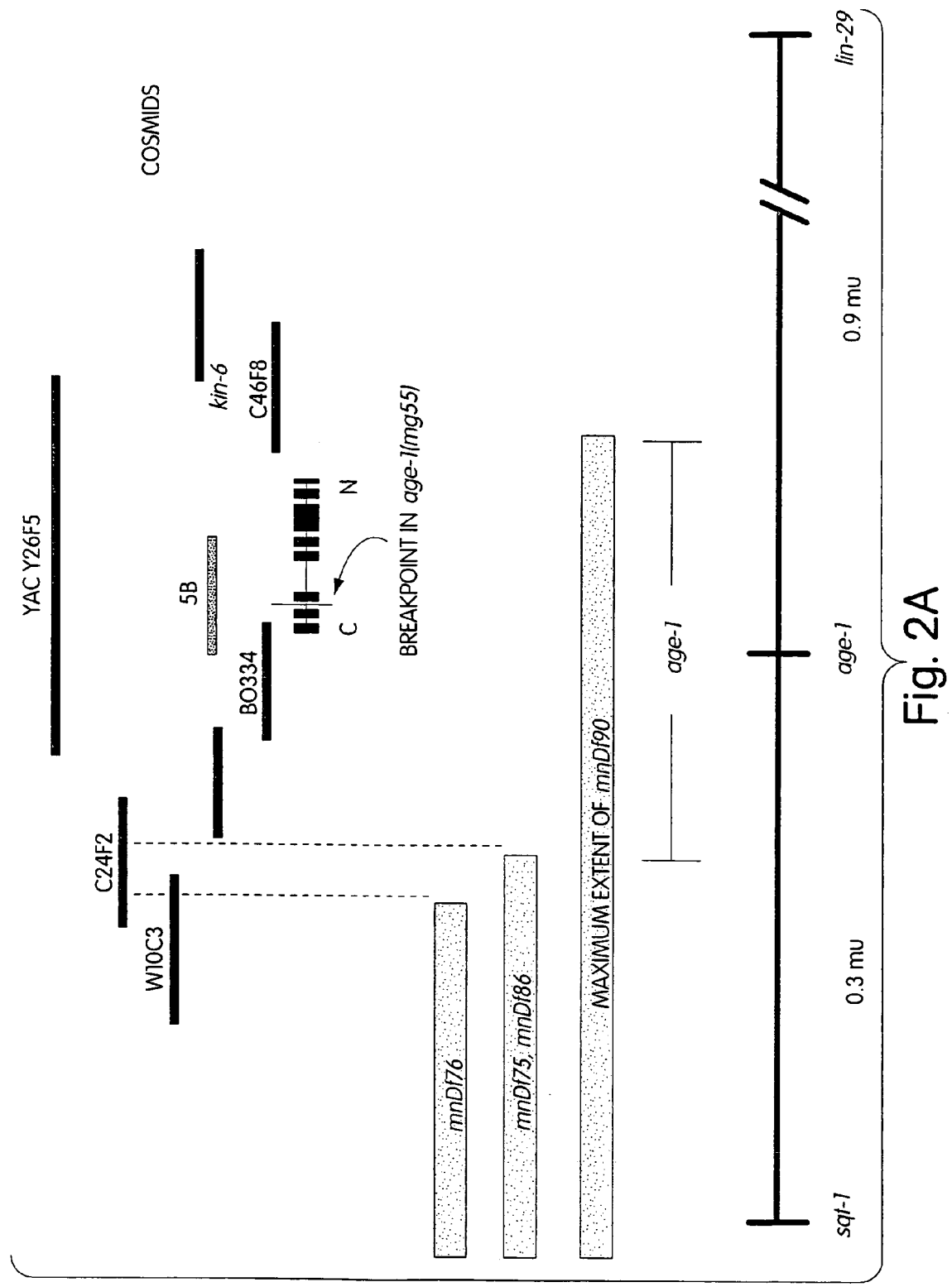

FIG. 2A is a diagram showing a physical/genetic map of the age-1 region, with genetic left oriented towards the left. age-1 is transcribed from right to left on this genetically oriented map. Cosmid and YAC clones in the sqt-1 lin-29 interval were placed by the *C. elegans* genome project. mnDf75, mnDf76, and mnDf86, all of which complement age-1 and fail to complement sqt-1, break in cosmid C24F2, as detected by Southern blots to Df/mnC1 DNAs using this cosmid as a probe (data not shown). The breakpoint in mnDf76, but not the breakpoints in mnDf75 or mnDf86, were also detected with cosmid W10C3, which partially overlaps C24F2 from the left. Thus age-1 must be located to the right of the breakpoints of these deficiencies. PCR analysis using kin-6 primers of embryos homozygous for mnDf90, which fails to complement both sqt-1 and age-1, shows that this deficiency deletes DNA to the left of kin-6, placing age-1 to the left of kin-6. Southern blots using cosmid B0334 as a probe detect a breakpoint in DNAs isolated from age-1(mg55)/mnC1 but not other age-1 alleles or other strains carrying mnC1. The age-1 transcript is not drawn to scale.

Figure 2B:
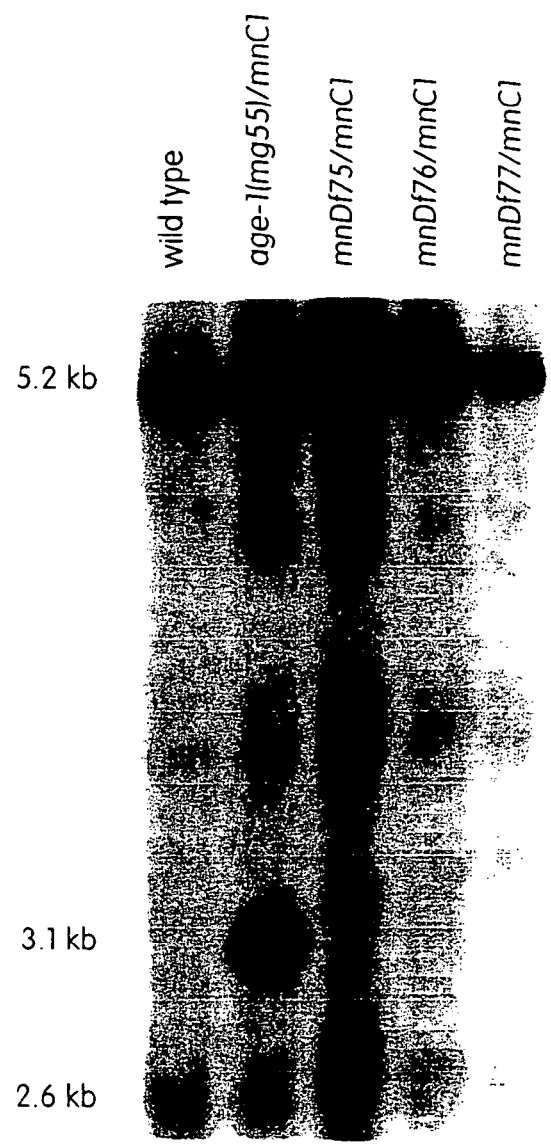

FIG. 2B is a photograph of a Southern blot analysis showing hybridization of HindIII-digested genomic DNA isolated from wild type (N2) (lane 1), age-1(mg55)/mnC1 (lane 2), and three Df/mnC1 control strains (lanes 3, 4, and 5) to a probe made from a 4 kb SalI subclone of phage 5B. This probe detects the region that encodes the C-terminal region of AGE-1. The strain bearing mg55 bears both a 5.2 kb HindIII fragment from the wild type age-1 allele on mnC1 and an altered 3.1 kb HindIII fragment from the age-1 (mg55) allele, indicating that the mg55 breakpoint was in or near the rightmost portion of cosmid B0334.

Figure 2C:
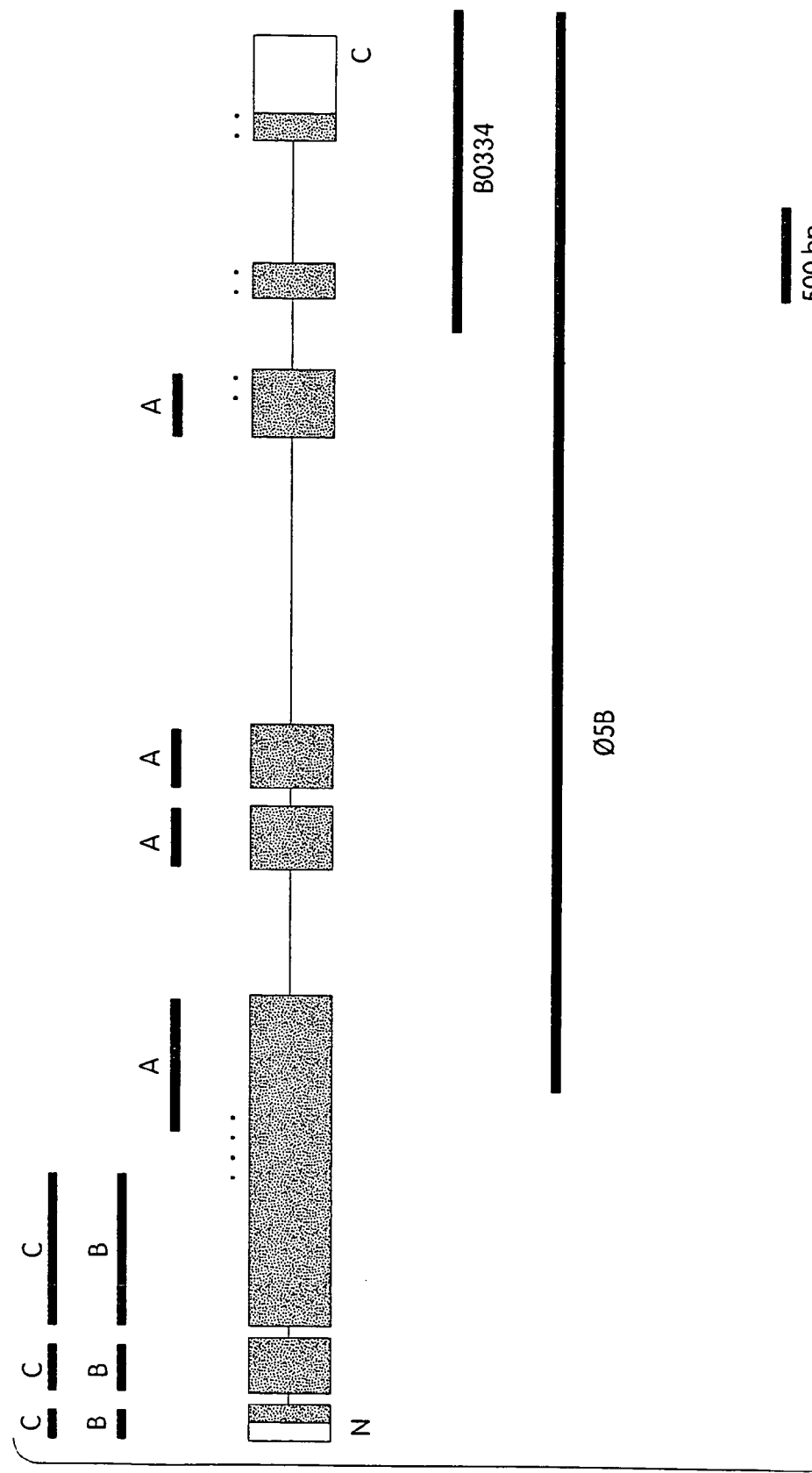

FIG. 2C is a diagram showing the gene structure of age-1 displayed next to the genomic and cDNA clones used to isolate the gene. The gene is flipped 180° relative to the genetic map, so that transcription is oriented left to right. White boxes indicate predicted untranslated regions. Periods indicate regions where sequence was obtained by RTPCR to verify splice junctions and to obtain the sequence joining cDNAs B and C to A. Independent cDNAs B and C occur in opposite orientations in the lambda vector and thus represent independent cloning events. They end within 30 bp of each other at their N termini, suggesting that they define the bona fide end of the age-1 MRNA. A third cDNA (not shown) ends within 5 bp of cDNA C, and is in the same orientation as cDNA C.

All the deficiencies indicated in FIGS. 2A, 2B, and 2C were isolated based on their failure to complement sqt-1. PCR using primer pairs from both sqt-1 and kin-6 was performed on single arrested L1 larvae (mnDf75, mnDf76, mnDf86) or from single dead eggs (mnDf90) laid by heterozygous deficiency/mnCl animals. To carry out the single worm/egg PCR protocol, single worms or eggs were picked into 2.5 µl of worm lysis buffer with proteinase K (50 mM KCl, 10 mM Tris pH 8.2, 2.5 mM Mg, 0.45% NP-40, 0.45% Tween-20, 0.01% gelatin, 60 µg/ml Proteinase K). Mineral oil was added, and tubes were frozen on dry ice, incubated at 60° C. for 1 hour, and at 95° C. for 15 minutes to lyse. 2.5 µl of worm lysis buffer was then added, and the reaction was divided into two PCR reactions for sqt-1 and kin-6 primers. The sqt-1 primers were: CTCTGGTTCATTTCCCAACC (SEQ ID NO: 3) and TGTAACTCACCTAGTCTTCG (SEQ ID NO: 4). The kin-6 primers were: AACAATTACAGGC-CGATCC (SEQ ID NO: 5) and ATGCCACGCAA-GAAACTCAC (SEQ ID NO: 6).

Phages B and C were isolated from the Barstaead random primer cDNA library (RBII) in lambda ACT. Phage A was isolated from the Ahringer staged embryonic library in lambda gt10. Phage Ø5B was isolated from the Browning genomic library in the lambda Dash vector. RNA for the RTPCR experiments was prepared using guanidinium thio-cyanate from mixed stage worms. cDNA preparation and anchor ligation were performed using the 5'-Amplifinder Race kit from Clontech. 36 µg of total RNA was reverse transcribed using a primer specific to age-1(sequence: GAAAAGATGGAATGTGACCG) (SEQ ID NO: 7). PCR was performed with the anchored primer from the kit and with a primer of sequence: ATCTGAAGCGTTCTTATATC (SEQ ID NO: 8) (which we later found to have an error). Nested PCR was performed using the anchored PCR primer again and internal primer: TGCTCCATTTTCTCCGATCC (SEQ ID NO: 9).

FIGS. 3-1 to 3-3 are the amino acid sequence of age-1 (SEQ ID NO: 1), as determined by sequencing cDNA clones, amplified reverse transcribed PCR fragments, and genomic regions described in FIG. 1. PCR generated templates were sequenced without subcloning and verified by sequencing multiple isolates. age-1 alleles were sequenced by PCR amplifying genomic regions and direct sequencing of templates without subdloning. Each mutation detected was verified by sequencing an independently amplified template. The AGE-1 sequence comparisons are to mouse p110α (accession number P42337) (SEQ ID NO: 10), human p110β (accession number P42338) (SEQ ID NO: 11), and human p110γ (accession number P48736) (SEQ ID NO: 12). Regions highlighted in gray and black were picked out by Prettybox, aligned by the Pileup program as having extended regions of high amino acid similarity (Program Manual for the Wisconsin Package, Version 8, September 1994, Genetics Computer Group, 575 Science Drive, Madison, Wis., USA 53711). Invariant amino acids in 3 of the 4 sequences are shown as black boxes. Similar amino acids in regions highlighted by 3 of 4 exact matches are highlighted in gray boxes. Allele lesions are shown above the amino acid which was altered. The asterisks (*) indicate a change to a stop codon. The brackets around age-1(mg55) show the region to which we mapped the age-1(mg55) breakpoint.

In these experiments, sequencing was carried out with the Promega fmol sequencing kit on cDNAs, RTPCR products, and PCR amplified genomic regions from the age-1 mutant alleles. The GCG programs, Translate, Pileup, and Prettybox, were then used to analyze the sequence.

FIGS. 4-1 and 4-2 are the nucleic acid sequence of an age-1 cDNA (SEQ ID NO: 2).

Figure 5:
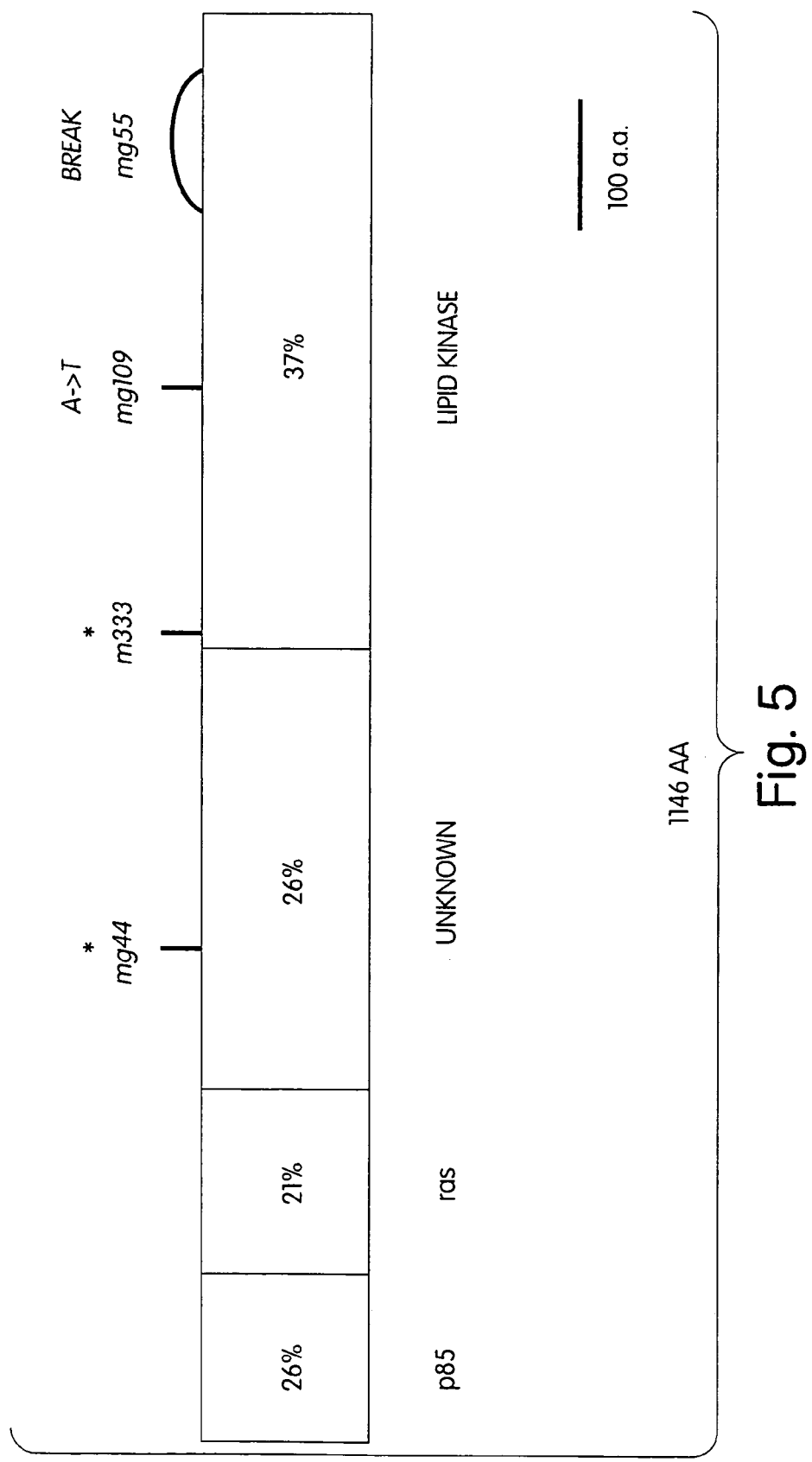

FIG. 5 is a diagram illustrating an AGE-1 lineup with mouse p110α. The diagram is to scale and extends over the 1146 amino acid AGE-1 sequence. Percentage identities shared between each domain of mouse p110α and the region of AGE-1 aligned with it by the Gap program are given. The domains labelled ras and p85 have been shown in p110α to bind ras and p85, respectively. The lipid kinase domain includes the region of AGE-1 that shares extensive homology with all lipid kinases. The approximate location of each point mutation is shown relative to the putative AGE-1 domains predicted by the Pileup program.

FIG. 6 is the amino acid sequence of an AGE-1 polypeptide (SEQ ID NO: 1). The highlighted amino acid positions are preferably unchanged in AGE-1 variants (based on their identity with amino acids in the human kinase p110α).

DETAILED DESCRIPTION

As described in more detail below, a pheromone-induced neurosecretory signaling system in *C. elegans* triggers developmental arrest and a dramatic increase in longevity at the dauer diapause stage. age-1 is a key gene in this neuroendocrine pathway whose activity is required both for non-arrested development and for normal senescence. As shown herein, age-1 encodes a member of the p110 family of phosphatidylinositol 3-kinase (PI 3-kinase) catalytic subunits. Four age-1 mutant alleles affect this PI 3-kinase homologue: two lesions are stop codons that truncate the protein at distinct locations N-terminal to the kinase domain and thus are likely to define the age-1 null phenotype. Maternal age-1 activity is specifically abrogated in one age-1 mutant which was isolated on the basis of its enhanced longevity. Lack of either maternal or zygotic age-1 gene activity confers long life-span but not developmental arrest whereas lack of both maternal and zygotic activity causes arrest at the dauer stage. These data suggest that decreased AGE-1-mediated phosphatidyl-inositol(3,4,5)$P_3$($PIP_3$) signaling leads to increased longevity, whereas complete lack of this signaling leads to developmental arrest.

Diapause in *C. elegans* and Other Organisms

In many animal phyla, neural signaling pathways couple sensory input to endocrine control of physiology and development. For example, many invertebrates arrest or alter their development in response to neuronal signals triggered by pheromones, light/dark cycles, or temperature (Tauber, M. J. et al., *Seasonal Adaptation of Insects* (New York, N.Y., 1986), Wilson, E. O., *The Insect Societies* (Cambridge, Mass., 1972)). The nematode *Caenhorabditis elegans* arrests development at the dauer diapause stage after particular sensory neurons are exposed to a dauer-inducing pheromone (Riddle, D. L. in *The Dauer Larva in The Nematode Caenorhabditis elegans*. (ed. Wood, W. B.) 393–412 (Cold Spring Harbor, N.Y., 1988)). The formation of a dauer larva includes behavioral, physiological, and morphological changes: dauer larvae suspend the molting cycle and germ line development, stop feeding but initiate dispersal behavior, and secrete a specialized sealed cuticle (Riddle, D. L. in *The Dauer Larva in The Nematode Caenorhabditis elegans*. (ed. Wood, W. B.) 393–412 (Cold Spring Harbor, N.Y., 1988)). When pheromone levels decrease, the dauer recovers and re-enters a normal feeding and molting cycle to produce fertile adult animals. Dauer formation also interrupts normal senescence in *C. elegans*. Dauer arrested larvae can survive more than eight times the life-span of non-dauer animals without affecting life-span after recovery from the dauer stage (Riddle, D. L. in *The Dauer Larva in The Nematode Caenorhabditis elegans*. (ed. Wood, W. B.) 393–412 (Cold Spring Harbor, N.Y., 1988)). Because of the global morphological and longevity changes associated with dauer formation, and by analogy with known endocrine control of diapause in other invertebrates (Williams, C. M., *Biol. Bull.* 103:120–138 (1952)), it is likely that a neuroendocrine pathway is coupled to the sensory neurons that detect the dauer pheromone.

Many mutations affecting dauer formation (daf mutations) have been isolated and characterized (Riddle, D. L. et al., *Nature* 290:668–671 (1981); Vowels, J. J. & Thomas, J. H., *Genetics* 130:105–123 (1992); Gottlieb, S. & Ruvkun, G., *Genetics* 137:107–120 (1994)). These fall into two main classes: dauer constitutive (daf-c) mutations, which cause animals to enter the dauer stage even in the absence of dauer-inducing pheromone, and dauer defective (daf-d) mutations, which prevent dauer formation even under conditions of high pheromone. The genes identified by these mutations have been ordered into a genetic epistasis pathway that is likely to represent the steps in the development or function of a neuroendocrine system composed of pheromone-sensing neurons, secretory cells, and target tissues (Riddle, D. L. et al., *Nature* 290:668–671 (1981); Vowels, J. J. & Thomas, J. H., *Genetics* 130:105–123 (1992); Gottlieb, S. & Ruvkun, G., *Genetics* 137:107–120 (1994); Thomas, J. H. et al., *Genetics* 134:1105–1117 (1993)). Two of these genes, daf-1 and daf-4 encode homologues of TGF-β receptors, implicating this signaling pathway in pheromone signal transduction (Georgi, L. L. et al., *Cell* 61:635–645 (1990); Estevez, M. et al., *Nature* 365:644–649 (1993)).

Among the many genes that mediate the function of the dauer neuroendocrine pathway, daf-2, daf-16, and daf-23 have been most directly implicated in regulation of longevity (Kenyon, C. et al., *Nature* 366:461–464 (1993); Larsen, P. L. et al., *Genetics* 139:1567–1583 (1995); Dorman, J. B. et al., *Genetics* 141:1399 (1995)). While strong daf-2 alleles and non-maternally rescued strong daf-23 alleles induce dauer formation in the absence of pheromone, temperature sensitive daf-2 alleles or maternally rescued daf-23 alleles increase longevity two to three fold without forming dauer larvae (Kenyon, C. et al., *Nature* 366:461–464 (1993); Larsen, P. L. et al., *Genetics* 139:1567–1583 (1995)). This suggests that the regulation of senescence can be decoupled from dauer formation. daf-16 mutations suppress both the dauer constitutive phenotype and the increase in longevity of daf-2 and daf-23 mutants (Kenyon, C. et al., *Nature* 366: 461–464 (1993); Larsen, P. L. et al., *Genetics* 139:1567–1583 (1995); Dorman, J. B. et al., *Genetics* 141: 1399 (1995)). Other daf mutations do not affect longevity, and are not efficiently suppressed by daf-16 mutations (Gottlieb, S. & Ruvkun, G., *Genetics* 137:107–120 (1994); Kenyon, C. et al., *Nature* 366:461–464 (1993); Larsen, P. L. et al., *Genetics* 139:1567–1583 (1995)). This genetic epistasis analysis suggests that the longevity-regulating daf-2, daf-16, daf-23 subpathway acts either downstream or in parallel to the TGF-β signaling component of the dauer pathway (Vowels, J. J. & Thomas, J. H., *Genetics* 130: 105–123 (1992); Gottlieb, S. & Ruvkun, G., *Genetics* 137: 107–120 (1994)).

AGE-1 Cloning and Analysis

Age-1(hx546) was isolated in a genetic screen for increased longevity (Klass, M., *Mech Aging Dev* 22:279–286 (1983); Friedman, D. B. & Johnson, T. E., *Genetics* 118:75–86 (1988)). Age-1(hx546) animals live twice as long as wild type, and this increase in longevity is suppressed by mutations in daf-16, like the increased longevity phenotype of daf-2 and daf-23 mutants (Kenyon, C. et al., *Nature* 366:461–464 (1993); Larsen, P. L. et al., *Genetics* 139:1567–1583 (1995); Dorman, J. B. et al., *Genetics* 141:1399 (1995)). Recently, Inoue and Thomas showed that at 27° C., a temperature above those routinely used in laboratory culture, age-1(hx546) has a dauer constitutive phenotype and fails to complement daf-23 dauer constitutive alleles. Because strong daf-23 alleles (e.g., m333 and mg44) are haploinsufficient at 27° C. (data not shown), complementation tests at that temperature are difficult to interpret. We complementation tested age-1(hx546) and dauer constitutive daf-23 alleles at lower temperatures where there is no such haploinsufficiency (FIG. 1). The results indicated that the age-1(hx546) fails to complement three daf-23 dauer constitutive mutant alleles, and maps to the same genetic interval. Age-1 was therefore assigned both the increased longevity allele (hx546) and the dauer constitutive mutant alleles (mg44, mg55, m333, mg109) previously referred to as daf-23 because the defining mutant allele was named age-1 (Klass, M., *Mech Aging Dev* 22:279–286 (1983); Friedman, D. B. & Johnson, T. E., *Genetics* 118: 75–86 (1988)). As shown below, age-1(hx546) is specifically defective in maternal age-1 gene activity, whereas the stronger dauer constitutive age-1 alleles are defective in both maternal and zygotic age-1 gene activity.

The age-1(mg44) null allele (see below) marked in cis with sqt-1(sc13) was used in this genetic analysis (FIG. 1). Animals bearing this age-1 allele normally arrest development as dauer larvae only if they receive no maternal or zygotic age-1 contribution (Gottlieb, S. & Ruvkun, G., *Genetics* 137:107–120 (1994)). For example, age-1(mg44) daughters of +/age-1(mg44) mothers develop into fertile adults that then produce a brood of arrested age-1(mg44) dauer larvae (FIG. 1). The age-1(hx546) mutation disrupts this maternal rescue: age-1(mg44) daughters of age-1(hx546)/age-1(mg44) mothers arrest development as dauers (FIG. 1). A similar lack of age-1(hx546) maternal rescue was observed for age-1(m333), another probable null allele (see below) and age-1(mg109) (data not shown). Consistent with disruption of only maternal age-1 expression by the age-1(hx546) mutation, a paternally contributed age-1(hx546) allele can zygotically rescue the dauer constitutive phenotype of progeny of age-1(mg44) homozygous mothers: age-1(hx546)/age-1(mg44) daughters of a mating of age-1(hx546) males to age-1(mg44)/age-1(mg44) hermaphrodites did not arrest development as dauer larvae, analogously to +/age-1(mg44) progeny from a mating to wild type males (FIG. 1). Genetic mapping placed age-1(hx546) in the same 1.2 map unit genetic interval as daf-23 (Gottlieb, S. & Ruvkun, G., *Genetics* 137:107–120 (1994)), between sqt-1 and lin-29 (FIG. 1).

As shown by previous genetic analysis (Gottlieb, S. & Ruvkun, G., *Genetics* 137:107–120 (1994)) and by the molecular analysis below, the dauer constitutive phenotype of most age-1 alleles is the probable null phenotype. age-1(hx546) was not dauer constitutive at most temperatures (Klass, M., *Mech Aging Dev* 22:279–286 (1983); Friedman, D. B. & Johnson, T. E., *Genetics* 118:75–86 (1988)), probably because the zygotic age-1 gene activity of this allele was sufficient to allow non-arrested development. This mutant may be long-lived because the decrease in maternally contributed age-1 causes a decrease in the rate of senescence. Similarly, lack of zygotic expression in maternally rescued age-1(m333) homozygous progeny of +/age-1(m333) parents also leads to life-span extension without dauer arrest (Larsen, P. L. et al., *Genetics* 139:1567–1583 (1995)). These animals had only maternal age-1 activity, since age-1(m333) is a null mutant (see below). Thus, normal senescence is likely to depend on both maternal and zygotic age-1 activity: in the absence of zygotic age-1 gene activity or reduced maternal age-1 gene activity, life-span increases. In the absence of both zygotic and maternal age-1 gene activity, animals arrest at the dauer stage.

The data illustrated in FIG. 1 is presented in tabular form below (Table 1).

TABLE 1

Regulation of lifespan and dauer formation by age-1

| | | | | Age phenotype | |
|---|---|---|---|---|---|
| Paternal genotype | Maternal genotype | Zygotic genotype | Dauer formation | Life-span (days) | Life-span relative to wild type |
| | +/+ | +/+ | non-dauer (1000) | 8.1 ± 0.2 (90) | 1.0 |
| | mg44/+ | mg44/mg44 | non-dauer (505)* | 20.7 ± 0.2 (26) | 2.6 |
| | mg44/mg44 | mg44/mg44 | non-dauer (505) | | |
| | hx546/hx546 | hx546/hx546 | non-dauer (1000) | 16.6 ± 1.0 (43) | 2.0 |
| +/+ | mg44/mg44 | mg44/+ | non-dauer (100) | 10.7 ± 0.5 (35) | 1.3 |
| hx546/hx546 | mg44/hx44 | hx546/mg44 | non-dauer (100) | 19.8 ± 1.1 (54) | 2.4 |
| | mg44/hx546 | mg44/mg44 | dauer (406) | | |

The age-1(mg44) chromosome is marked in cis with sqt-1(sc13), and age-1(mg44)/+ strains have the mnC1 balances chromosome as the + chromosome. Lifespan at 25° C. is measured from the L4 stage to the last day that animals respond to light touch, and is presented as the mean ± s.e. Note that sqt-1(sc13) age-1(mg44) progeny of age-1(hx546)/sqt-1(sc13) age-1(mg44) form dauer larvae with 100% penetrance at 25° C. This is the same as control age-1(mg44) daughters of age-1(mg44) parents. The dauer larvae produced in both cases have the dark intestine, pharyngeal and cuticular remodelling, and arrest of the moulting cycle characteristic of this stage[3-5]. In contrast, 99% of sqt-1(sc13) age-1(mg44) progeny of sqt-1(sc13) age1(mg44)/+ do not form dauer larvae, showing that maternal age-1 activity is sufficient to allow non-dauer development. These animals live 2.6-fold longer than wild-type worms. Zygotic age-1(+) in the absence of maternal age-1 can supply sufficient activity for normal lifespan and non-dauer development, but zygotic age-1(hx546) does not supply sufficient activity for normal longevity. Similar results were observed with other age-1 alleles m333 and mg109 (data not shown). We three-factor mapped age-1(hx546) to the 1.2 map unit sqt-1 lin-29 interval. Of 20 recombinants in this interval, 4 were between sqt-1 and age-1(hx546), and 16 were between age-1 and lin-29. This shows that age-1(hx546) maps to the same genetic interval as age-1(mg44). Consistent with this mapping, Sqt recombinants of the genotype sqt-1(sc13) age-1(mg44)/sqt-1(sc13) age-1(hx546) were isolated from sqt-1(sc13) age-1(mg44)/age-1(hx546) worms. Wild-type or age-1(hx546) males were mated into sqt-1(sc13) age-1(mg44) hermaphrodites. Cross progeny were picked to separate plates at 25° C. and F$_2$ progeny were scored 3 days later. For genetic mapping, recombinants were picked from age-1(hx546)/sqt-1(sc13) lin29(n333) hermaphrodites. Recombinants were tested for failure to maternally complement age-1(m333) for dauer formation at 25° C.
*1% of these worms form dauer larvae, and 20% become sterile adults.

The 1.2 map unit sqt-1 lin-29 interval to which age-1 maps consists of approximately 700 kb of DNA on 4 contigs (Gottlieb, S. & Ruvkun, G., *Genetics* 137:107–120 (1994)). The physical and genetic maps were correlated in this region by using five small chromosome II deficiencies, some of which complement and some of which fail to complement mutations in age-1. Age-1 was determined to lie to the right of or on cosmid C24F2 because mnDf75, mnDf76, and mnDf86 deficiencies, which fail to complement sqt-1 but complement age-1, had breakpoints detectable by cosmid C24F2 (FIG. 2A). Age-1 was physically mapped to the left of the cloned marker kin-6 (which lies on cosmid C46F8) by using PCR to determine that dead eggs homozygous for mnDf90, a deficiency which fails to complement both sqt-1 and age-1, contained the DNA for kin-6 whereas they deleted sqt-1(FIG. 2A). These deficiencies mapped age-1 to an approximately 240 kb interval between cosmid clones C24F2 and C46F8. Using cosmids from this interval as probes on Southern blots, we searched for a breakpoint associated with the age-1(mg55) gamma-ray-induced allele. Because age-1(mg55) showed pseudolinkage to chromosome I in genetic crosses (Gottlieb, S. & Ruvkun, G., *Genetics* 137:107–120 (1994)), this allele was suspected to be associated with a translocation and was the best a priori candidate allele to show a breakpoint in age-1. Probes from cosmid B0334 and probes from genomic clones overlapping the rightmost region in B0334 detected a novel breakpoint in age-1(mg55)/mnC1 but not in control DNAs carrying the same mnC1 balancer chromosome (FIGS. 2B and 2C).

The *C. elegans* Genome Project (Sulston, J. et al., *Nature* 356:37–41 (1992)) has sequenced cosmid B0334. Analysis of the DNA sequence in the 4 kb region that detected the age-1(mg55) breakpoint revealed two putative exons that showed strong sequence identity with the last 88 amino acids of mammalian phosphatidylinositol 3-kinase (PI 3-kinase) p110 catalytic subunit (Hiles, I. D. et al., *Cell* 70:419–429 (1992)). The region to the right of B0334 expected to contain the rest of age-1 was not cloned in cosmids or phage by the *C. elegans* genome project. We isolated genomic phage and cDNA clones extending to the right from B0334 and used anchored polymerase chain reaction (PCR) of reverse transcribed RNA to isolate and determine the sequence of the coding region of age-1(FIG. 2C). To confirm the splicing pattern of age-1, reverse transcription PCR (RTPCR) was used in conjunction with genomic sequencing of predicted splice junctions. The sequence predicted by cDNA clones and anchored PCR was further confirmed by sequencing genomic fragments corresponding to the predicted coding sequence. Because three independent cDNA clones end within 30 base pairs of each other and because these encode a protein coextensive with mammalian p110 (see below), we concluded that the assembled age-1 cDNA was likely to be complete. The nucleic acid sequence of the *C. elegans* age-1 cDNA is shown in FIG. 4.

Analysis of the age-1 DNA sequence revealed an open reading frame of 1185 amino acids. The age-1 open reading frame bears four in-frame methionine residues that are potential translation start sites. While the second methionine shows a closer match to the *C. elegans* translation initiation consensus, the Kozak translation initiation rules favor the first methionine in an MRNA (Kozak, M., *Nucleic Acids Research* 15:8125–8132 (1987); Kozak, M., *Proc. Natl Acad. Sci.* 92:2662–2666 (1995); Krause, M. in *Caenorhabditis elegans Modern Biological Analysis of an Organism* (ed. Epstein, H. F. & Shakes, D. C.) 483–512 (San Diego, Calif., 1995)). Numbering from the first initiation codon, age-1 was predicted to encode a 1146 amino acid protein (FIGS. 3 and 6). The age-1 genomic region encoding this protein was sequenced from four age-1 EMS-induced alleles, m333, mg44, mg109, and hx546, revealing G->A point mutations (the predicted mutation from EMS mutagenesis) within this coding region in DNA isolated from three age-1 alleles (see below). No change in the age-1(hx546) coding region or 3' UTR was detected. Because this mutation specifically affects maternal age-1 activity, it may be located in a flanking transcriptional regulatory region not yet sequenced. Thus four age-1 mutations, mg55, m333, mg44, and mg109 affect this open reading frame, endorsing its assignment to age-1 gene activity.

The AGE-1 protein is closely related to a family of mammalian phosphatidylinositol 3-kinase (PI 3-kinase) p110 catalytic subunits (Hiles, I. D. et al., Cell 70:419–429 (1992); Kapeller R. & Cantley, L. C., Bioessays 16:565–576 (1994)). PI 3-kinases generate a membrane-localized signaling molecule, phosphatidylinositol $P_3$ ($PIP_3$) (Riddle, D. L. in The Dauer Larva in The Nematode Caenorhabditis elegans. (ed. Wood, W. B.) 393–412 (Cold Spring Harbor, N.Y., 1988); Williams, C. M., Biol. Bull. 103:120–138 (1952); Riddle, D. L. et al., Nature 290:668–671 (1981)) that is thought to transduce signals from upstream receptors to as yet unknown effector molecules (Kapeller R. & Cantley, L. C., Bioessays 16:565–576 (1994)). There are three known PI 3-kinase types. The $\alpha$ and $\beta$ p110 types are targeted to activated receptor kinases by the regulatory p85 or p55 subunits (Kapeller R. & Cantley, L. C., Bioessays 16:565–576 (1994)). These regulatory subunits have SH2 domains that recognize phosphorylated tyrosines on those receptors and other proteins (Kapeller R. & Cantley, L. C., Bioessays 16:565–576 (1994); Liscovitch, M. & Cantley, L. C., Cell 81:659–662 (1995); Carpenter, C. L. et al., Molecular and Cellular Biology 13:1657–65 (1993); Dhand, R. et al., EMBO Journal 13:511–21 (1994); Pons, S. et al., Molecular and Cellular Biology 15:4453–65 (1995)). The p110$\alpha$ or p110$\beta$ types bind to p85 via their N-terminal 130 amino acids (Kapeller R. & Cantley, L. C., Bioessays 16:565–576 (1994); Liscovitch, M. & Cantley, L. C., Cell 81:659–662 (1995); Carpenter, C. L., et al., Molecular and Cellular Biology 13:1657–65 (1993)). The p110$\alpha$ can phosphorylate p85 subunits as well as lipids (Carpenter, C. L. et al., Molecular and Cellular Biology 13:1657–65 (1993); Dhand, R. et al., EMBO Journal 13:511–21 (1994)); thus PI 3-kinases may also transduce signals via a protein kinase cascade. A third type of p110 subunit, p110$\gamma$, binds to heterotrimeric G-proteins, and presumably couples indirectly to serpentine receptors (Stoyanov, B. et al., Science 269:690–3 (1995)).

Gap and Blast analysis (Program Manual for the Wisconsin Package, Version 8 Sep. 1994, Genetics Computer Group, 575 Science Drive, Madison, Wis., USA 53711) indicated that AGE-1 is 29.6% identical to mouse p110$\alpha$, 29.8% identical to human p110$\beta$, and 28.0% identical to human p110$\gamma$. Large segments of AGE-1 show up to 42% sequence identity to the p110 PI-3 kinase proteins in the kinase and upstream domains conserved in lipid kinases (FIGS. 3 and 5). Comparison of AGE-1 to the p110 proteins in the N-terminal 130 amino acids that mediate p 110 $\alpha$ and $\beta$ interaction with p85 (Dhand, R. et al., EMBO Journal 13:511–21 (1994)) showed that AGE-1 is more related to p110$\alpha$ (22.0% identity) than to p110$\beta$ (17.1% identity) or p110$\gamma$ (9.8% identity) in this region. Many of the amino acid residues in this region that are conserved between AGE-1 and p110$\alpha$, are also conserved between p110$\alpha$ and p110$\beta$, which share 45% amino acid identity in the region (FIG. 3).

The random probability of alignment of AGE-1 with these p110 kinases is extremely low: $e^{-113}$ for p110$\alpha$, $e^{-101}$ for p110$\beta$, and $e^{-93}$ for p110$\gamma$ (versus, for example, a probability of random alignment with PI 4-kinase of $e^{-22}$ or to DNA repair kinases of $e^{-8}$). The regions conserved in AGE-1 suggest that this protein may couple to a p85-like tyrosine kinase adaptor rather than to a $G_{\beta\gamma}$ like adaptor protein. However, over the entire protein, mouse p110$\alpha$ is more similar to the other mammalian p110 classes than to AGE-1(mouse p110$\alpha$ is 42.0% identical to human p110$\beta$ and 34.5% identical to human p110$\gamma$, vs. 30.1% identical to AGE-1), suggesting that AGE-1 may be a divergent PI 3-kinase class.

The age-1 maternal effect dauer constitutive mutations are probable null alleles. age-1(mg44) is a Trp405 Amber mutation that truncates AGE-1 upstream of the kinase domain and most of the conserved regions (FIG. 3). This mutation is a good candidate to define the age-1 null phenotype. The age-1(m333) mutation is Trp659Opal that also truncates the AGE-1 protein upstream of most conserved domains, and is also a likely null allele. The age-1(mg55) breakpoint removes the C terminal portion of the kinase domain from the AGE-1 protein and age-1 3'UTR FIG. 2A). Age-1 (mg109) causes an Ala845Thr substitution in a region of the protein that is conserved among AGE-1 and mammalian PI 3-kinases (FIG. 3). Both AGE-1 and mammalian p110$\alpha$ have an Ala at this position, whereas p110$\beta$ and $\gamma$ have Lys at this position (FIG. 3). The high degree of conservation and the severity of the age-1(mg109) phenotype suggests that this region performs an essential function in AGE-1.

All of these age-1 alleles, including those that are predicted to truncate the AGE-1 protein, show a dauer constitutive phenotype which can be rescued by wild type maternal gene activity. In addition, the age-1(m333) allele, which is a probable null allele, shows a dramatic longevity increase when maternal but not zygotic age-1 gene activity is supplied (Larsen, P. L. et al., Genetics 139:1567–1583 (1995)). These data show that the AGE-1 PI 3-kinase homologue functions in the particular signaling pathway that controls dauer developmental arrest and senescence, and are not consistent with a more general AGE-1 requirement. In addition, this shows that maternal AGE-1-mediated phosphatidylinositol signaling is sufficient to rescue lack of zygotic AGE-1 signaling for arrest at the dauer stage but not for decreased senescence. Because in age-1(hx546), reduced maternal AGE-1 phosphatidylinositol signaling also leads to increased longevity, these data suggest that normal senescence depends on phosphatidylinositol signaling from both maternal and zygotic AGE-1.

The strong sequence similarity that AGE-1 shares with mammalian PI 3-kinases suggests a variety of possible roles that $PIP_3$ signaling could play in regulating dauer development and senescence. In mammals, PI 3-kinase signaling has been implicated in neural development as well as in hormonal signaling. Nerve growth factor signaling from the Trk kinase receptor and neurite outgrowth in PC12 cells are inhibited by the PI 3-kinase inhibitor wortmannin (Kimura, K. et al., J. Biol. Chem. 269:18961–7 (1994); Yao, R. & Cooper, G. M., Science 267:2003–6 (1995)). PI 3-kinase has also been implicated in histamine secretion by mast cells (Yano, H. et al., J. Biol. Chem. 268:25846–25856 (1993)) and in signal transduction downstream of the metabolic control hormone insulin (Levy-Toledano, R. et al., J. Biol. Chem. 269:31178–31182 (1994)). Thus, there are precedents for PI 3-kinase function at many of the steps that are likely to be required in a neuroendocrine pathway, including development and differentiation of neurons and target tissues, secretory events, and signal transduction in target tissues.

AGE-1-mediated $PIP_3$ signaling could function in the development of the dauer neurosecretory pathway or in the transduction of pheromone signal in the pathway. Genetic epistasis analysis suggests that age-1 may function downstream of the daf genes involved in sensory processing of the dauer pheromone signal, for example in the development or function of secretory neurons or target tissues (Gottlieb, S. & Ruvkun, G., Genetics 137:107–120 (1994)). The observation that age-1 null mutants are maternally rescued for dauer arrest is consistent with an early age-1 role. The dauer pheromone is normally detected during the L1 stage (Riddle, D. L. in *The Dauer Larva in The Nematode Caenorhabditis elegans*. (ed. Wood, W. B.) 393–412 (Cold Spring Harbor, N.Y., 1988)), suggesting that if the maternally supplied AGE-1 functions in pheromone signal transduction, the age-1 mRNA, protein, or phosphatidylinositol signal itself must perdure from the germ line until this stage. If age-1 mediates development of this pathway, it would be expected to function during embryogenesis when the neurons and target tissues likely to function in the dauer neuroendocrine pathway are generated.

The longevity phenotype of age-1 mutants suggests a direct function of phosphatidylinositol signaling in senescence. Disruption of age-1 gene activity confers long life span in the absence of dauer entry, suggesting that the longevity of these mutants is not a simple consequence of dauer entry. More likely, reduced PI 3-kinase activity triggers a subset of the dauer program that includes a decrease in the rate of senescence but not developmental arrest. Free radical byproducts of aerobic metabolism have been suggested to contribute to senescence by directly damaging a variety of essential molecules, including DNA, proteins, and lipids (Finch, C. E., *Longevity, Senescence, and the Genome* (Chicago, Ill. 1990)). If phosphatidylinositol signaling from AGE-1 normally regulates the level of free radicals, then decreases in age-1 gene activity in mutants or dauer larvae could lead to increased longevity. In fact, age-1 mutants and dauer larvae show increased levels of catalase and superoxide dismutase and resistance to free radical generating drugs and treatments (Larsen, P., *Proc. Natl. Acad. Sci.* 90:8905–8909 (1993); VanFleteren, J. R., *Biochem. J.* 292: 605–608 (1993)). Interestingly, a wortmannin-sensitive PI-3 kinase is necessary in the production of superoxide radicals in bacterial killing by mammalian neutrophils (Okada, T. et al., *J Biol. Chem.* 269:3563–3567 (1994); Thelen, M. et al., *Proc. Natl. Acad. Sci.* 91:4960–4 (1994)).

The identification of age-1 as a PI 3-kinase suggests that other genes in the dauer genetic pathway could identify the in vivo downstream targets of $PIP_3$ signaling. daf-2 functions at the same point as age-1 in the dauer and senescence epistasis pathway (Vowels, J. J. & Thomas, J. H., *Genetics* 130:105–123 (1992); Gottlieb, S. & Ruvkun, G., *Genetics* 137:107–120 (1994); Kenyon, C. et al., *Nature* 366:461–464 (1993); Larsen, P. L. et al., *Genetics* 139:1567–1583 (1995); Dorman, J. B. et al., *Genetics* 141:1399 (1995)). DAF-2 could be a downstream positively-regulated target of $PIP_3$ signaling, a PI 3-kinase regulatory subunit such as p85 or p55, or an upstream receptor. Candidates for positively-regulated downstream targets of $PIP_3$ signaling have been detected biochemically (Liscovitch & L. C. Cantley, L., *Cell* 77:324–34 (1994); Toker, A. et al., *The Journal of Biological Chemistry* 269:32358–67 (1994); Akimoto, K. et al., *The EMBO Journal* 15:788–798 (1996); Jones, P. F. et al., *Proc. Natl. Acad. Sci.* 80:4171–5 (1991); Franke, T. F. et al., *Cell* 81:727–736 (1995); Burgering, B. M. T. & Coffer, P. J., *Nature* 376:599–602 (1995)); the in vivo function of such candidates would be validated by detection of daf gene homologues. No negatively regulated targets of $PIP_3$ signaling have been detected biochemically. Genetic data indicates that daf-16 may be a negatively regulated target of $PIP_3$ signaling; the increase in longevity and arrest at the dauer stage in the age-1 mutant that we argue here results from a loss in $PIP_3$ signaling is suppressed by mutations in daf-16 (Vowels, J. J. & Thomas, J. H., *Genetics* 130:105–123 (1992); Gottlieb, S. & Ruvkun, G., *Genetics* 137:107–120 (1994); Kenyon, C. et al., *Nature* 366:461–464 (1993); Larsen, P. L. et al., *Genetics* 139:1567–1583 (1995); Dorman, J. B. et al., *Genetics* 141:1399 (1995)). These observations suggest that under conditions of non-arrested normally senescing growth, the small membrane-bound $PIP_3$ product of AGE-1 negatively regulates DAF-16 activity to control life span in *C. elegans*.

Cloning Mammalian AGE-1 Polypeptides

Based on our isolation of a novel AGE-1 gene and cDNA, the isolation of additional mammalian AGE-1 nucleic acid sequences, including human AGE-1, is made possible using the sequence described herein and standard techniques. In particular, using all or a portion of the AGE-1 sequence, one may readily design AGE-1 oligonucleotide probes, including degenerate oligonucleotide probes (i.e., a mixture of all possible coding sequences for a given amino acid sequence). These oligonucleotides may be based upon the sequence of either strand of the DNA. Exemplary probes or primers for isolating mammalian AGE-1 sequences preferably correspond to conserved blocks of amino acids, for example, amino acids 852–864 (IFKNGDDLRQDML) (SEQ ID NO: 13) or amino acids 1111–1116 (HIDFGH) (SEQ ID NO: 14) of FIG. 6 (SEQ ID NO: 1). General methods for designing and preparing such probes are provided, for example, in Ausubel et al., *Current Protocols in Molecular Biology*, 1996, Wiley & Sons, New York, N.Y.; and *Guide to Molecular Cloning Techniques*, 1987, S. L. Berger and A. R. Kimmel, eds., Academic Press, New York. These oligonucleotides are useful for AGE-1 gene isolation, either through their use as probes for hybridizing to AGE-1 complementary sequences or as primers for various polymerase chain reaction (PCR) cloning strategies. If a PCR approach is utilized, the primers are optionally designed to allow cloning of the amplified product into a suitable vector.

Hybridization techniques and procedures are well known to those skilled in the art and are described, for example, in Ausubel et al., supra, and *Guide to Molecular Cloning Techniques*, supra. If desired, a combination of different oligonucleotide probes may be used for the screening of the recombinant DNA library. The oligonucleotides are, for example, labelled with $^{32}P$ using methods known in the art, and the detectably-labelled oligonucleotides are used to probe filter replicas from a recombinant DNA library. Recombinant DNA libraries (for example, human cDNA libraries) may be prepared according to methods well known in the art, for example, as described in Ausubel et al., supra, or may be obtained from commercial sources.

For detection or isolation of closely related AGE-1 sequences, high stringency hybridization conditions may be employed; such conditions include hybridization at about 42° C. and about 50% formamide; a first wash at about 65° C., about 2×SSC, and 1% SDS; followed by a second wash at about 65° C. and about 0.1% SDS, 1×SSC. Lower stringency conditions for detecting AGE-1 genes having less sequence identity to the AGE-1 gene described herein include, for example, hybridization at about 42° C. in the absence of formamide; a first wash at about 42° C., about 6×SSC, and about 1% SDS; and a second wash at about 50° C., about 6×SSC, and about 1% SDS.

As discussed above, AGE-1 oligonucleotides may also be used as primers in PCR cloning strategies. Such PCR methods are well known in the art and described, for example, in PCR *Technology,* H. A. Erlich, ed., Stockton Press, London, 1989; PCR *Protocols: A Guide to Methods and Applications*, M. A. Innis, D. H. Gelfand, J. J. Sninsky, and T. J. White, eds., Academic Press, Inc., New York, 1990; and Ausubel et al., supra. Again, sequences corresponding to conserved regions in the AGE-1 sequence (for example, those regions described above) are preferred for use in isolating mammalian AGE-1 sequences.

AGE-1 Polypeptide Expression

In general, AGE-1 polypeptides according to the invention may be produced by transformation of a suitable host cell with all or part of an AGE-1-encoding cDNA fragment (e.g., one of the cDNAs described above) in a suitable expression vehicle.

Those skilled in the field of molecular biology will understand that any of a wide variety of expression systems may be used to provide the recombinant protein. The precise host cell used is not critical to the invention. The AGE-1 polypeptide may be produced in a prokaryotic host (e.g., *E. coli*) or in a eukaryotic host (e.g., *Saccharomyces cerevisiae*, insect cells, e.g., Sf9 or Sf21 cells, or mammalian cells, e.g., COS 1, NIH 3T3, or HeLa cells). Such cells are available from a wide range of sources (e.g., the American Type Culture Collection, Rockland, Md.; also, see, e.g., Ausubel et al., supra). The method of transformation or transfection and the choice of expression vehicle will depend on the host system selected. Transformation and transfection methods are described, e.g., in Ausubel et al. (supra); expression vehicles may be chosen from those provided, e.g., in *Cloning Vectors: A Laboratory Manual* (P. H. Pouwels et al., 1985, Supp. 1987).

One preferred expression system is the baculovirus system (using, for example, Sf9 cells and the method of Ausubel et al., supra). Another baculovirus system makes use of the vector pBacPAK9 and is available from Clontech (Palo Alto, Calif.).

Alternatively, an AGE-1 polypeptide is produced in a mammalian system, for example by a stably-transfected mammalian cell line. A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the AGE-1 protein is cloned into an expression vector which includes the dihydrofolate reductase (DHFR) gene. Integration of the plasmid and, therefore, the AGE-1 protein-encoding gene into the host cell chromosome is selected for by inclusion of 0.01–300 μM methotrexate in the cell culture medium (as described in Ausubel et al., supra). This dominant selection may be accomplished in most cell types. Recombinant protein expression may be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra). Any of the host cells described above or, preferably, a DHFR-deficient CHO cell line (e.g., CHO DHFR⁻ cells, ATCC Accession No. CRL 9096) are among the host cells preferred for DHFR selection of a stably-transfected cell line or DHFR-mediated gene amplification.

In yet other alternative approaches, the AGE-1 polypeptide is produced in vivo or, preferably, in vitro using a T7 system (see, for example, Ausubel et al., supra, or other standard techniques).

Once the recombinant AGE-1 protein is expressed, it is isolated, e.g., using affinity chromatography. In one example, an anti-AGE-1 protein antibody (e.g., produced as described herein) may be attached to a column and used to isolate the AGE-1 protein. Lysis and fractionation of AGE-1 protein-harboring cells prior to affinity chromatography may be performed by standard methods (see, e.g., Ausubel et al., supra).

Once isolated, the recombinant protein can, if desired, be further purified, e.g., by high performance liquid chromatography (see, e.g., Fisher, *Laboratory Techniques In Biochemistry And Molecular Biology*, eds., Work and Burdon, Elsevier, 1980).

Polypeptides of the invention, particularly short AGE-1 polypeptide fragments, may also be produced by chemical synthesis (e.g., by the methods described in *Solid Phase Peptide Synthesis*, 2nd ed., 1984 The Pierce Chemical Co., Rockford, Ill.).

These general techniques of polypeptide expression and purification may also be used to produce and isolate useful AGE-1 fragments or analogs (described herein).

Anti-AGE-1 Antibodies

Using the AGE-1 polypeptide described above, anti-AGE-1 antibodies have been produced as follows. An AGE-1 cDNA fragment encoding amino acids 1089–1164 was fused to GST, and the fusion protein produced in *E. coli* by standard techniques. The fusion protein was then purified on a glutathione column, also by standard techniques, and was used to immunize rabbits. The antisera obtained was then itself purified on a GST-AGE-1 affinity column by the method of Finney and Ruvkun (*Cell* 63:895–905, 1990). This antisera was shown to specifically identify GST-AGE-1 by Western blotting.

Other AGE-1-specific antibodies may be produced by this or alternative techniques. For example, the AGE-1 polypeptides described herein (or immunogenic fragments or analogs) may be used to raise other polyclonal antisera or monoclonal antibodies; one particular alternative immunogenic fragment is represented by AGE-1 amino acids 550 to 965. Polypeptides for antibody production may be produced by recombinant or peptide synthetic techniques (see, e.g., *Solid Phase Peptide Synthesis*, supra; Ausubel et al., supra).

For polyclonal antisera, the peptides may, if desired, be coupled to a carrier protein, such as KLH as described in Ausubel et al, supra. The KLH-peptide is mixed with Freund's adjuvant and injected into guinea pigs, rats, or preferably rabbits. Antibodies may be purified by any method of peptide antigen affinity chromatography.

Alternatively, monoclonal antibodies may be prepared using an AGE-1 polypeptide (or immunogenic fragment or analog) and standard hybridoma technology (see, e.g., Kohler et al., *Nature* 256:495, 1975; Kohler et al., *Eur. J. Immunol.* 6:511, 1976; Kohler et al., *Eur. J. Immunol.* 6:292, 1976; Hammerling et al., *In Monoclonal Antibodies and T Cell Hybridomas*, Elsevier, N.Y., 1981; Ausubel et al., supra).

Once produced, polyclonal or monoclonal antibodies are tested for specific AGE-1 recognition by Western blot or immunoprecipitation analysis (by the methods described in Ausubel et al., supra). Antibodies which specifically recognize AGE-1 are considered to be useful in the invention; such antibodies may be used, e.g., in an immunoassay to measure or monitor the level of AGE-1 produced by a mammal or to screen for compounds which modulate AGE-1 production. Anti-AGE-1 antibodies may also be used to identify cells that express the AGE-1 gene.

Samples obtained from the AGE-1 nonsense alleles, m333 and mg44 (described above), provide useful negative controls for antisera specificity.

Identification and Administration of Molecules that Modulate AGE-1 Expression or Activity Isolation of an AGE-1 cDNA and knowledge of its involvement in the aging process also facilitates the identification of molecules which decrease AGE-1 expression or activity (i.e., AGE-1 antagonists). According to one approach, AGE-1 expression is measured following the addition of antagonist molecules to the culture medium of AGE-1-expressing cells. Alternatively, the candidate antagonists may be directly administered to animals (for example, nematodes or mice) and used to screen for antagonists.

AGE-1 expression is then measured, for example, by standard Northern blot analysis (Ausubel et al., supra) using an AGE-1 nucleic acid (or fragment) as a hybridization probe. The level of AGE-1 expression in the presence of the candidate molecule is compared to the level measured for the same cells in the same culture medium or test animal, but in the absence of the candidate molecule. Preferred modulators for anti-aging purposes are those which cause a decrease in AGE-1 expression.

Alternatively, the effect of candidate modulators on expression may be measured at the level of AGE-1 protein production using the same general approach in combination with standard immunological detection techniques, such as Western blotting or immunoprecipitation with an AGE-1-specific antibody (for example, the AGE-1 antibody described herein). Again, useful anti-aging modulators are identified as those which produce a decrease in AGE-1 polypeptide production.

Candidate modulators may be purified (or substantially purified) molecules or may be one component of a mixture of compounds (e.g., an extract or supernatant obtained from cells). In a mixed compound assay, AGE-1 expression is tested against progressively smaller subsets of the candidate compound pool (e.g., produced by standard purification techniques, e.g., HPLC or FPLC; Ausubel et al., supra) until a single compound or minimal compound mixture is demonstrated to modulate AGE-1 expression.

Alternatively, or in addition, candidate compounds may be screened for those which antagonize native or recombinant AGE-1 activity. In a preferred approach, kinase activity (for example, PI 3-kinase activity) in the presence of, or after treatment with, a candidate compound is compared to activity in its absence under equivalent conditions. Again, such a screen may begin with a pool of candidate compounds, from which one or more useful modulator compounds are isolated in a step-wise fashion.

Kinase activity may be measured by any standard assay, for example, it may be measured by monitoring the ability of the enzyme to transfer $^{32}$P-ATP to a PIP substrate on a TLC plate (as described, for example, by Whitman et al., Nature 322:644–646, 1988), or it may be measured by the method of Kimura et al. (J. Biol. Chem. 269:18961–18967, 1994). If desired, prior to assaying activity, the enzyme may be isolated from a sample, for example, by immunoprecipitation with an AGE-1-specific antibody. The AGE-1 mutants described herein (for example, mg44, m333, and mg109) have reduced activity in these in vitro assays and may be used as control samples.

Candidate AGE-1 antagonists include peptide as well as non-peptide molecules (e.g., peptide or non-peptide molecules found, e.g., in a cell extract, mammalian serum, or growth medium on which mammalian cells have been cultured). Because the most likely AGE-1 substrate is $PIP_2$ and its product $PIP_3$, drugs that mimic the transition state between $PIP_2$ and $PIP_3$ (so called, transition analogs) are good candidates for compounds which down-regulate the AGE-1-mediated synthesis of $PIP_3$, and thereby increase longevity. Because both the AGE-1 substrate and product are membrane bound molecules, drugs that interfere with AGE-1 action may be hydrophobic, decreasing or eliminating problems commonly associated with membrane permeability.

Antagonists found to be effective at the level of cellular AGE-1 expression or activity may be confirmed as useful in animal models (for example, nematodes or mice).

A molecule which promotes a decrease in AGE-1 expression or AGE-1 activity is considered particularly useful in the invention; such a molecule may be used, for example, as a therapeutic to decrease the level or activity of native, cellular AGE-1 and thereby increase the longevity of the host animal (for example, human).

An AGE-1 antagonist for therapeutic use may be administered with a pharmaceutically-acceptable diluent, carrier, or excipient, in unit dosage form. Conventional pharmaceutical practice may be employed to provide suitable formulations or compositions to administer AGE-1 to patients. Although intravenous administration is preferred, any appropriate route of administration may be employed, for example, parenteral, subcutaneous, intramuscular, intracranial, intraorbital, ophthalmic, intraventricular, intracapsular, intraspinal, intracisternal, intraperitoneal, intranasal, aerosol, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found in, for example, "Remington's Pharmaceutical Sciences." Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for AGE-1 antagonists include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, treatment with an AGE-1 antagonist may be combined with any other anti-aging therapy.

AGE-1 Pesticides

AGE-1 antagonists may also be used as novel pesticides, for example, to control insects or nematodes. Because AGE-1 controls diapause, compounds which antagonize its action may be used to trigger diapause inappropiately, with a concomitant suspension of feeding behavior and reproduction (Tauber et al., *Seasonal Adaptation of Insects*, 1986, New York, N.Y., Oxford University Press, p. 411). Such pesticides, which target invertebrate diapause events, are useful for enhancing agricultural production with fewer human health hazards than current neurotransmitter-based pesticides.

Determination of Longevity

Due to their role in aging, AGE-1 polypeptides and nucleic acid sequences are useful for determining the longevity of an organism (for example, a human). In particular, because decreased AGE-1 correlates with increased longevity, a decrease in the level of AGE-1 production or activity provides an indication that a host organism will age more slowly or have an increased life-span. Levels of AGE-1 expression or its activity may be assayed by any standard technique.

For example, expression in a biological sample may be monitored by standard Northern blot analysis or may be aided by PCR (see, e.g., Ausubel et al., supra; *PCR Technology: Principles and Applications for DNA Amplification*, ed., H. A. Ehrlich, Stockton Press, NY).

Alternatively, immunoassays may be used to detect or monitor the level of AGE-1 protein. AGE-1-specific polyclonal or monoclonal antibodies (produced as described above) may be used in any standard immunoassay format (e.g., ELISA, Western blot, or RIA assay) to measure AGE-1 polypeptide levels; again comparison is to wild-type AGE-1 levels, and a decrease in AGE-1 production is indicative of increased longevity. Examples of immunoassays are described, e.g., in Ausubel et al., supra. Immunohistochemical techniques may also be utilized for AGE-1 detection. For example, a tissue sample may be obtained from an individual, and a section stained for the presence of AGE-1 using an anti-AGE-1 antibody and any standard detection system (e.g., one which includes a secondary antibody conjugated to horseradish peroxidase). General guidance regarding such techniques can be found in, e.g., Bancroft and Stevens (*Theory and Practice of Histological Techniques*, Churchill Livingstone, 1982) and Ausubel et al. (supra).

Mismatch detection assays also provide the opportunity to detect AGE-1 mutations and thereby determine longevity. This type of approach may also be used to detect AGE-1 variants in prenatal screens.

Finally, a combined method may be employed that begins with an evaluation of AGE-1 protein production (for example, by immunological techniques) and also includes a nucleic acid-based detection technique designed to identify more subtle AGE-1 mutations (for example, point mutations). A number of standard mismatch detection assays are available to those skilled in the art, and any preferred technique may be used. By this approach, mutations in AGE-1 may be detected that either result in loss of AGE-1 expression or loss of AGE-1 biological activity. In a variation of this combined method, AGE-1 activity (rather than production) is measured as kinase activity using any appropriate kinase assay system (for example, the assays of Whitman et al., Nature 322:644–646 (1988); or Kimura et al., J. Biol. Chem. 269:18961–18967 (1994)).

AGE-1 Interacting Polypeptides

The isolation of AGE-1 sequences also facilitates the identification of polypeptides which interact with the AGE-1 protein. Such polypeptide-encoding sequences are isolated by any standard two hybrid system (see, for example, Fields et al., *Nature* 340:245–246 (1989); Yang et al., *Science* 257:680–682 (1992); Zervos et al., *Cell* 72:223–232 (1993)). For example, all or a part of the AGE-1 sequence may be fused to a DNA binding domain (such as the GAL4 or LexA DNA binding domain). After establishing that this fusion protein does not itself activate expression of a reporter gene (for example, a lacZ or LEU2 reporter gene) bearing appropriate DNA binding sites, this fusion protein is used as an interaction target. Candidate interacting proteins fused to an activation domain (for example, an acidic activation domain) are then co-expressed with the AGE-1 fusion in host cells, and interacting proteins are identified by their ability to contact the AGE-1 sequence and stimulate reporter gene expression. False positive interactions are eliminated by carrying out a control experiment with an unrelated tester protein fused to an equivalent activation domain (or, if desired, a large panel of such tester proteins).

Once AGE-1 protein-protein interactions are identified, compounds may be screened for those which disrupt the interaction. These compounds provide good candidates for AGE-1 antagonists and may be tested or confirmed by any of the approaches described above. Compounds identified by this method may be used for any of the above-described purposes.

OTHER EMBODIMENTS

In other embodiments, the invention includes any protein which is substantially identical to the AGE-1 polypeptide of FIG. 6 (SEQ ID NO: 1); such homologs include other substantially pure naturally-occurring mammalian AGE-1 polypeptides (for example, the human AGE-1 polypeptide) as well as allelic variants; natural mutants; induced mutants; proteins encoded by DNA that hybridizes to the AGE-1 DNA sequence of FIG. 4 (SEQ ID NO: 2) under high stringency conditions or, less preferably, under low stringency conditions (e.g., washing at 2×SSC at 40° C. with a probe length of at least 40 nucleotides); and proteins specifically bound by antisera directed to an AGE-1 polypeptide.

The invention further includes analogs of any naturally-occurring AGE-1 polypeptide. Analogs can differ from the naturally-occurring AGE-1 protein by amino acid sequence differences, by post-translational modifications, or by both. Analogs of the invention will generally exhibit at least 50%, more preferably 60%, and most preferably 85% or even 95% identity with a naturally-occurring AGE-1 amino acid sequence. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring AGE-1 polypeptide by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, *Molecular Cloning: A Laboratory Manual* (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., β or γ amino acids.

In addition to full-length polypeptides, the invention also includes AGE-1 polypeptide fragments. As used herein, the term "fragment," means at least 20 contiguous amino acids, preferably at least 30 contiguous amino acids, more preferably at least 50 contiguous amino acids, and most preferably at least 60 to 80 or more contiguous amino acids. Fragments of AGE-1 polypeptides can be generated by methods known to those skilled in the art or may result from normal protein processing (e.g., removal of amino acids from the nascent polypeptide that are not required for biological activity or removal of amino acids by alternative mRNA splicing or alternative protein processing events). Preferable fragments according to the invention include, without limitation, amino acids amino acids 387–641, 387–1146, 1–130, 1–150, 1–658, or 1–404 of FIG. 6 (SEQ ID NO: 1).

For certain purposes, all or a portion of the AGE-1 polypeptide sequence may be fused to another protein (for example, by recombinant means). In one example, AGE-1 may be fused to the green fluorescent protein, GFP (Chalfie et al., *Science* 263:802–805, 1994). Such a fusion protein is useful, for example, for monitoring the expression level of AGE-1 in vivo (for example, by fluorescence microscopy) following treatment with candidate or known AGE-1 antagonists.

The methods of the invention may be used to determine longevity or screen for AGE-1 modulatory compounds in any mammal, for example, humans, domestic pets, or livestock. Where a non-human mammal is treated or diagnosed, the AGE-1 polypeptide, nucleic acid, or antibody employed is preferably specific for that species.

All publications and patent applications mentioned in this specification are herein incorporated by reference to the same extent as if each independent publication or patent application was specifically and individually indicated to be incorporated by reference.

Other embodiments are within the following claims.

What is claimed is:

1. A purified and isolated DNA which encodes an AGE-1 polypeptide, said polypeptide comprising the sequence of SEQ ID NO: 1.

2. A vector comprising the purified and isolated AGE-1 DNA of claim 1.

3. An isolated cell comprising the purified and isolated AGE-1 DNA of claim 1.

4. A method of producing a recombinant AGE-1 polypeptide, said method comprising the steps of:
   (a) providing a cell transformed with the DNA of claim 1 encoding an AGE-1 polypeptide, said DNA being expressed in the cell;
   (b) culturing the transformed cell under conditions for expressing the DNA; and
   (c) isolating the recombinant AGE-1 polypeptide.

5. A recombinant AGE-1 polypeptide produced according to the method of claim 4.

6. A method of identifying an AGE-1 modulatory compound that is capable of decreasing the expression of an AGE-1 gene, said method comprising the steps of:
 (a) providing a nematode cell expressing its endogenous AGE-1 DNA;
 (b) contacting said nematode cell with a candidate compound;
 (c) isolating a sample from said nematode cell after contacting; and
 (d) measuring AGE-1 gene expression in said sample, wherein a decrease in AGE-1 gene expression in said sample isolated from said nematode cell following contact with said candidate compound, compared to AGE-1 gene expression in a sample isolated from a nematode cell that is not contacted with said candidate compound, identifies said candidate compound as a compound that is capable of decreasing AGE-1 gene expression.

7. A method of identifying an AGE-1 modulatory compound that is capable of decreasing AGE-1 PI-3 kinase activity, said method comprising the steps of:
 (a) providing a nematode cell expressing the AGE-1 polypeptide of claim 1;
 (b) contacting the nematode cell with a candidate compound;
 (c) isolating a sample from said nematode cell after contacting; and
 (d) measuring PI-3 kinase activity in said sample, wherein a decrease in AGE-1 PI-3 kinase activity in said sample isolated from said nematode cell following contact with said candidate compound, compared to AGE-1 PI-3 kinase activity in a sample isolated from a nematode cell that is not contacted with said candidate compound, identifies said candidate compound as a compound that is capable of decreasing AGE-PI3 kinase activity.

8. The method of claim 6 or 7, wherein said method is carried out in a nematode.

9. The method of claim 6 or 7, wherein said method involves assaying AGE-1 PI 3-kinase activity in vitro.

* * * * *

UNITED STATES PATENT AND TRADEMARK OFFICE
CERTIFICATE OF CORRECTION

PATENT NO. : 7,094,889 B2  
APPLICATION NO. : 08/908453  
DATED : August 22, 2006  
INVENTOR(S) : Ruvkun et al.

It is certified that error appears in the above-identified patent and that said Letters Patent is hereby corrected as shown below:

On the Cover Page, References Cited, in OTHER PUBLICATIONS:
  In Leung et al., replace "Leung TK et al." with --Leung, T.K. et al.,--;
  In Miyazaki et al., replace "Miyazaki K et al." with --Miyazaki, K. et al.,--;
  In Clements et al., replace "Clements JE et al." with --Clements, J.E. et al.,--;
  In Hiles et al., replace "Hiles et al" with --Hiles et al.,--;
  In Goode et al., replace "Goode et al" with --Goode et al.,--;
  In Wilson et al., replace "Wilson et al" with --Wilson et al.,--;
  In Jazwinski, replace "Jazwinski, s. Michal," with --Jazwinski, S. Michal,--.

Column 1, Line 49, replace "*Caenhorabditis*" with --*Caenorhabditis*--.

Column 7, Line 52, replace "subdloning" with --subcloning--.

Column 8,
  Line 15, replace "labelled" with --labeled--;
  Line 58, replace "*Caenhorabditis*" with --*Caenorhabditis*--.

Column 11, Line 49, replace "remodelling" with --remodeling--.

Column 16,
  Line 53, replace "labelled" with --labeled--;
  Line 54, replace "labelled" with --labeled--.

Column 18, Line 54, replace "et al," with --et al.,--.

Column 21, Line 2, replace "inappropiately" with --inappropriately--.

Signed and Sealed this

Twelfth Day of June, 2007

JON W. DUDAS  
*Director of the United States Patent and Trademark Office*

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 1146 amino acids
      (B) TYPE: amino acid
      (C) STRANDEDNESS: unknown
      (D) TOPOLOGY: linear (ii) MOLECULE TYPE: protein (xi) SEQUENCE DESCRIPTION: SEQ ID NO:1:

Met His Val Asn Ile Leu His Pro Gln Leu Gln Thr Met Val Glu Gln
1               5                   10                  15

Trp Gln Met Arg Glu Arg Pro Ser Leu Glu Thr Glu Asn Gly Lys Gly
            20                  25                  30

Ser Leu Leu Leu Glu Asn Glu Gly Val Ala Asp Ile Ile Thr Met Cys
        35                  40                  45

Pro Phe Gly Glu Val Ile Ser Val Val Phe Pro Trp Phe Leu Ala Asn
    50                  55                  60

Val Arg Thr Ser Leu Glu Ile Lys Leu Ser Asp Phe Lys His Gln Leu
65                  70                  75                  80

Phe Glu Leu Ile Ala Pro Met Lys Trp Gly Thr Tyr Ser Val Lys Pro
                85                  90                  95

Gln Asp Tyr Val Phe Arg Gln Leu Asn Asn Phe Gly Glu Ile Glu Val
            100                 105                 110

Ile Phe Asn Asp Asp Gln Pro Leu Ser Lys Leu Glu Leu His Gly Thr
        115                 120                 125

Phe Pro Met Leu Phe Leu Tyr Gln Pro Asp Gly Ile Asn Arg Asp Lys
    130                 135                 140

Glu Leu Met Ser Asp Ile Ser His Cys Leu Gly Tyr Ser Leu Asp Lys
145                 150                 155                 160

Leu Glu Glu Ser Leu Asp Glu Leu Arg Gln Phe Arg Ala Ser Leu
                165                 170                 175

Trp Ala Arg Thr Lys Lys Thr Cys Leu Thr Arg Gly Leu Glu Gly Thr
            180                 185                 190

Ser His Tyr Ala Phe Pro Glu Glu Gln Tyr Leu Cys Val Gly Glu Ser

```
            195                 200                 205
Cys Pro Lys Asp Leu Glu Ser Lys Val Lys Ala Ala Lys Leu Ser Tyr
    210                 215                 220

Gln Met Phe Trp Arg Lys Arg Lys Ala Glu Ile Asn Gly Val Cys Glu
225                 230                 235                 240

Lys Met Met Lys Ile Gln Ile Glu Phe Asn Pro Asn Glu Thr Pro Lys
                245                 250                 255

Ser Leu Leu His Thr Phe Leu Tyr Glu Met Arg Lys Leu Asp Val Tyr
            260                 265                 270

Asp Thr Asp Pro Ala Asp Glu Gly Trp Phe Leu Gln Leu Ala Gly
        275                 280                 285

Arg Thr Thr Phe Val Thr Asn Pro Asp Val Lys Leu Thr Ser Tyr Asp
    290                 295                 300

Gly Val Arg Ser Glu Leu Glu Ser Tyr Arg Cys Pro Gly Phe Val Val
305                 310                 315                 320

Arg Arg Gln Ser Leu Val Leu Lys Asp Tyr Cys Arg Pro Lys Pro Leu
                325                 330                 335

Tyr Glu Pro His Tyr Val Arg Ala His Glu Arg Lys Leu Ala Leu Asp
            340                 345                 350

Val Leu Ser Val Ser Ile Asp Ser Thr Pro Lys Gln Ser Lys Asn Ser
        355                 360                 365

Asp Met Val Met Thr Asp Phe Arg Pro Thr Ala Ser Leu Lys Gln Val
    370                 375                 380

Ser Leu Trp Asp Leu Asp Ala Asn Leu Met Ile Arg Pro Val Asn Ile
385                 390                 395                 400

Ser Gly Phe Asp Phe Pro Ala Asp Val Asp Met Tyr Val Arg Ile Glu
                405                 410                 415

Phe Ser Val Tyr Val Gly Thr Leu Thr Leu Ala Ser Lys Ser Thr Thr
            420                 425                 430

Lys Val Asn Ala Gln Phe Ala Lys Trp Asn Lys Glu Met Tyr Thr Phe
        435                 440                 445

Asp Leu Tyr Met Lys Asp Met Pro Pro Ser Ala Val Leu Ser Ile Arg
    450                 455                 460

Val Leu Tyr Gly Lys Val Lys Leu Lys Ser Glu Glu Phe Glu Val Gly
465                 470                 475                 480

Trp Val Asn Met Ser Leu Thr Asp Trp Arg Asp Glu Leu Arg Gln Gly
                485                 490                 495

Gln Phe Leu Phe His Leu Trp Ala Pro Glu Pro Thr Ala Asn Arg Ser
            500                 505                 510

Arg Ile Gly Glu Asn Gly Ala Arg Ile Gly Thr Asn Ala Ala Val Thr
        515                 520                 525

Ile Glu Ile Ser Ser Tyr Gly Gly Arg Val Arg Met Pro Ser Gln Gly
    530                 535                 540

Gln Tyr Thr Tyr Leu Val Lys His Arg Ser Thr Trp Thr Glu Thr Leu
545                 550                 555                 560

Asn Ile Met Gly Asp Asp Tyr Glu Ser Cys Ile Arg Asp Pro Gly Tyr
                565                 570                 575

Lys Lys Leu Gln Met Leu Val Lys Lys His Glu Ser Gly Ile Val Leu
            580                 585                 590

Glu Glu Asp Glu Gln Arg His Val Trp Met Trp Arg Arg Tyr Ile Gln
        595                 600                 605

Lys Gln Glu Pro Asp Leu Leu Ile Val Leu Ser Glu Leu Ala Phe Val
    610                 615                 620
```

-continued

```
Trp Thr Asp Arg Glu Asn Phe Ser Glu Leu Tyr Val Met Leu Glu Lys
625                 630                 635                 640

Trp Lys Pro Pro Ser Val Ala Ala Leu Thr Leu Leu Gly Lys Arg
            645                 650                 655

Cys Thr Asp Arg Val Ile Arg Lys Phe Ala Val Glu Lys Leu Asn Glu
                660                 665                 670

Gln Leu Ser Pro Val Thr Phe His Leu Phe Ile Leu Pro Leu Ile Gln
            675                 680                 685

Ala Leu Lys Tyr Glu Pro Arg Ala Gln Ser Glu Val Gly Met Met Leu
        690                 695                 700

Leu Thr Arg Ala Leu Cys Asp Tyr Arg Ile Gly His Arg Leu Phe Trp
705                 710                 715                 720

Leu Leu Arg Ala Glu Ile Ala Arg Leu Arg Asp Cys Asp Leu Lys Ser
                725                 730                 735

Glu Glu Tyr Arg Arg Ile Ser Leu Leu Met Glu Ala Tyr Leu Arg Gly
            740                 745                 750

Asn Glu Glu His Ile Lys Ile Ile Thr Arg Gln Val Asp Met Val Asp
        755                 760                 765

Glu Leu Thr Arg Ile Ser Thr Leu Val Lys Gly Met Pro Lys Asp Val
770                 775                 780

Ala Thr Met Lys Leu Arg Asp Glu Leu Arg Ser Ile Ser His Lys Met
785                 790                 795                 800

Glu Asn Met Asp Ser Pro Leu Asp Pro Val Tyr Lys Leu Gly Glu Met
                805                 810                 815

Ile Ile Asp Lys Ala Ile Val Leu Gly Ser Ala Lys Arg Pro Leu Met
            820                 825                 830

Leu His Trp Lys Asn Lys Asn Pro Lys Ser Asp Leu His Leu Pro Phe
        835                 840                 845

Cys Ala Met Ile Phe Lys Asn Gly Asp Asp Leu Arg Gln Asp Met Leu
850                 855                 860

Val Leu Gln Val Leu Glu Val Met Asp Asn Ile Trp Lys Ala Ala Asn
865                 870                 875                 880

Ile Asp Cys Cys Leu Asn Pro Tyr Ala Val Leu Pro Met Gly Glu Met
                885                 890                 895

Ile Gly Ile Ile Glu Val Val Pro Asn Cys Lys Thr Ile Phe Glu Ile
            900                 905                 910

Gln Val Gly Thr Gly Phe Met Asn Thr Ala Val Arg Ser Ile Asp Pro
        915                 920                 925

Ser Phe Met Asn Lys Trp Ile Arg Lys Gln Cys Gly Ile Glu Asp Glu
    930                 935                 940

Lys Lys Lys Ser Lys Lys Asp Ser Thr Lys Asn Pro Ile Glu Lys Lys
945                 950                 955                 960

Ile Asp Asn Thr Gln Ala Met Lys Lys Tyr Phe Glu Ser Val Asp Arg
                965                 970                 975

Phe Leu Tyr Ser Cys Val Gly Tyr Ser Val Ala Thr Tyr Ile Met Gly
            980                 985                 990

Ile Lys Asp Arg His Ser Asp Asn Leu Met Leu Thr Glu Asp Gly Lys
        995                 1000                1005

Tyr Val His Ile Asp Phe Gly His Ile Leu Gly His Gly Lys Thr Lys
    1010                1015                1020

Leu Gly Ile Gln Arg Asp Arg Gln Pro Phe Ile Leu Thr Glu His Phe
025                 1030                1035                1040
```

```
Met Thr Val Ile Arg Ser Gly Lys Ser Val Asp Gly Asn Ser His Glu
              1045                1050                1055
Leu Gln Lys Phe Lys Thr Leu Cys Val Glu Ala Tyr Glu Val Met Trp
              1060                1065            1070
Asn Asn Arg Asp Leu Phe Val Ser Leu Phe Thr Leu Met Leu Gly Met
        1075                1080                1085
Glu Leu Pro Glu Leu Ser Thr Lys Ala Asp Leu Asp His Leu Lys Lys
      1090                1095                1100
Thr Leu Phe Cys Asn Gly Glu Ser Lys Glu Glu Ala Arg Lys Phe Phe
105                1110                1115                1120
Ala Gly Ile Tyr Glu Glu Ala Phe Asn Gly Ser Trp Ser Thr Lys Thr
              1125                1130                1135
Asn Trp Leu Phe His Ala Val Lys His Tyr
              1140                1145
```

(2) INFORMATION FOR SEQ ID NO:2:

(i) SEQUENCE CHARACTERISTICS:
        (A) LENGTH: 3504 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:2:

```
CGGAAGCCAT GGAGCTCGAG ATCTGATTGC TGGACACGGA CGGAACTCCG ACGTATCTCG      60
CAGATGCATG TTAACATTTT ACATCCACAA CTGCAAACGA TGGTCGAGCA GTGGCAAATG     120
CGAGAACGCC CATCGCTGGA GACCGAGAAT GGCAAAGGAT CGCTGCTCCT GGAAAATGAA     180
GGTGTCGCAG ATATCATCAC TATGTGTCCA TTCGGAGAAG TTATTAGTGT AGTATTTCCG     240
TGGTTTCTTG CAAATGTGCG AACATCGCTA GAAATCAAGC TATCAGATTT CAAACATCAA     300
CTTTTCGAAT TGATTGCTCC GATGAAGTGG GGAACATATT CCGTAAAGCC ACAGGATTAT     360
GTGTTCAGAC AGTTGAATAA TTTCGGCGAA ATTGAAGTTA TATTTAACGA CGATCAACCC     420
CTGTCGAAAT TAGAGCTCCA CGGCACTTTC CCAATGCTTT TTCTCTACCA ACCTGATGGA     480
ATAAACAGGG ATAAAGAATT AATGAGTGAT ATAAGTCATT GTCTAGGATA CTCACTGGAT     540
AAACTGGAAG AGAGCCTCGA TGAGGAACTC CGTCAATTTC GTGCTTCTCT CTGGGCTCGT     600
ACGAAGAAAA CGTGCTTGAC ACGTGGACTT GAGGGTACCA GTCACTACGC GTTCCCCGAA     660
GAACAGTACT TGTGTGTTGG TGAATCGTGC CCGAAAGATT TGGAATCAAA AGTCAAGGCT     720
GCCAAGCTGA GTTATCAGAT GTTTTGGAGA AAACGTAAAG CGGAAATCAA TGGAGTTTGC     780
GAGAAAATGA TGAAGATTCA AATTGAATTC AATCCGAACG AAACTCCGAA ATCTCTGCTT     840
CACACGTTTC TCTACGAAAT GCGAAAATTG GATGTATACG ATACCGATGA TCCTGCAGAT     900
GAAGGATGGT TCTTCAATT GGCTGGACGT ACCACGTTTG TTACAAATCC AGATGTCAAA     960
CTTACGTCTT ATGATGGTGT CCGTTCGGAA CTGGAAAGCT ATCGATGCCC TGGATTCGTT    1020
GTTCGCCGAC AATCACTAGT CCTCAAAGAC TATTGTCGCC CAAAACCACT CTACGAACCA    1080
CATTATGTGA GAGCACACGA ACGAAAACTT GCTCTAGACG TGCTCAGCGT GTCTATAGAT    1140
AGCACACCAA AACAGAGCAA GAACAGTGAC ATGGTTATGA CTGATTTTCG TCCGACAGCT    1200
TCACTCAAAC AAGTTTCACT TTGGGACCTT GACGCGAATC TTATGATACG GCCTGTGAAT    1260
ATTTCTGGAT TCGATTTCCC GGCCGACGTG GATATGTACG TTCGAATCGA ATTCAGTGTA    1320
TATGTGGGGA CACTGACGCT GGCATCAAAA TCTACAACAA AAGTGAATGC TCAATTTGCA    1380
```

```
AAATGGAATA AGGAAATGTA CACTTTTGAT CTATACATGA AGGATATGCC ACCATCTGCA    1440

GTACTCAGCA TTCGTGTTTT GTACGGAAAA GTGAAATTAA AAAGTGAAGA ATTCGAAGTT    1500

GGTTGGGTAA ATATGTCCCT AACCGATTGG AGAGATGAAC TACGCAAGG ACAATTTTTA    1560

TTCCATCTGT GGGCTCCTGA ACCGACTGCC AATCGTAGTA GGATCGGAGA AAATGGAGCA    1620

AGGATAGGCA CCAACGCAGC GGTTACAATT GAAATCTCAA GTTATGGTGG TAGAGTTCGA    1680

ATGCCGAGTC AAGGACAATA CACATATCTC GTCAAGCACC GAAGTACTTG ACGGAAACT    1740

TTGAATATTA TGGGTGATGA CTATGAGTCG TGTATCAGAG ATCCAGGATA TAAGAAGCTT    1800

CAGATGCTTG TCAAGAAGCA TGAATCTGGA ATTGTATTAG AGGAAGATGA ACAACGTCAT    1860

GTCTGGATGT GGAGGAGATA CATTCAAAAG CAGGAGCCTG ATTTGCTCAT TGTGCTCTCC    1920

GAACTCGCAT TTGTGTGGAC TGATCGTGAG AACTTTTCCG AGCTCTATGT GATGCTTGAA    1980

AAATGGAAAC CGCCGAGTGT GGCAGCCGCG TTGACTTTGC TTGGAAAACG TTGCACGGAT    2040

CGTGTGATTC GAAAGTTTGC AGTGGAGAAG TTGAATGAGC AGCTGAGCCC GGTCACATTC    2100

CATCTTTTCA TATTGCCTCT CATACAGGCG TTGAAGTACG AACCGCGTGC TCAATCGGAA    2160

GTTGGAATGA TGCTCTTGAC TAGAGCTCTC TGCGATTATC GAATTGGACA TCGACTTTTC    2220

TGGCTGCTCC GTGCAGAGAT TGCTCGTTTG AGAGATTGTG ATCTGAAAAG TGAAGAATAT    2280

CGCCGTATCT CACTTCTGAT GGAAGCTTAC CTCCGTGGAA ATGAAGAGCA CATCAAGATC    2340

ATCACCCGAC AAGTTGACAT GGTTGATGAG CTCACACGAA TCAGCACTCT TGTCAAAGGA    2400

ATGCCAAAAG ATGTTGCTAC GATGAAACTG CGTGACGAGC TTCGATCGAT TAGTCATAAA    2460

ATGGAAAATA TGGATTCTCC ACTGGATCCT GTGTACAAAC TGGGTGAAAT GATAATCGAC    2520

AAAGCCATCG TCCTAGGAAG TGCAAAACGT CCGTTAATGC TTCACTGGAA GAACAAAAAT    2580

CCAAAGAGTG ACCTGCACCT TCCGTTCTGT GCAATGATCT TCAAGAATGG AGACGATCTT    2640

CGCCAGGACA TGCTTGTTCT TCAAGTTCTC GAAGTTATGG ATAACATCTG GAAGGCTGCA    2700

AACATTGATT GCTGTTTGAA CCCGTACGCA GTTCTTCCAA TGGGAGAAAT GATTGGAATT    2760

ATTGAAGTTG TGCCTAATTG TAAAACAATA TTCGAGATTC AAGTTGGAAC AGGATTCATG    2820

AATACAGCAG TTCGGAGTAT TGATCCTTCG TTTATGAATA AGTGGATTCG GAAACAATGC    2880

GGAATTGAAG ATGAAAAGAA GAAAAGCAAA AAGGACTCTA CGAAAAATCC CATCGAAAAG    2940

AAGATTGATA ATACTCAAGC CATGAAGAAA TATTTTGAAA GTGTCGATCG ATTCCTATAC    3000

TCGTGTGTTG GATATTCAGT TGCCACGTAC ATAATGGGAA TCAAGGATCG TCACAGTGAT    3060

AATCTGATGC TCACTGAAGA TGGAAAATAT GTCCACATTG ATTTCGGTCA CATTTTGGGA    3120

CACGGAAAGA CCAAACTTGG GATCCAGCGA GATCGTCAAC CGTTTATTCT AACCGAACAC    3180

TTTATGACAG TGATTCGATC GGGTAAATCT GTGGATGGAA ATTCGCATGA GCTACAAAAA    3240

TTCAAAACGT TATGCGTCGA AGCCTACGAA GTAATGTGGA ATAATCGAGA TTTGTTCGTT    3300

TCCTTGTTCA CCTTGATGCT CGGAATGGAG TTGCCTGAGC TGTCGACGAA AGCGGATTTG    3360

GATCATTTGA AGAAAACCCT CTTCTGCAAT GGAGAAAGCA AAGAAGAAGC GAGAAAGTTT    3420

TTCGCTGGAA TCTACGAAGA AGCCTTCAAT GGATCATGGT CTACCAAAAC GAATTGGCTC    3480

TTCCACGCAG TCAAACACTA CTGA                                          3504

(2) INFORMATION FOR SEQ ID NO:3:

(i) SEQUENCE CHARACTERISTICS:
             (A) LENGTH: 20 base pairs
             (B) TYPE: nucleic acid
```

(C) STRANDEDNESS: single
            (D) TOPOLOGY: linear (ii) MOLECULE TYPE: Other (xi) SEQUENCE DESCRIPTION: SEQ ID NO:3:

CTCTGGTTCA TTTCCCAACC                                              20

(2) INFORMATION FOR SEQ ID NO:4:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:4:

TGTAACTCAC CTAGTCTTCG                                              20

(2) INFORMATION FOR SEQ ID NO:5:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:5:

AACAATTACA GGCCGATCC                                               19

(2) INFORMATION FOR SEQ ID NO:6:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:6:

ATGCCACGCA AGAAACTCAC                                              20

(2) INFORMATION FOR SEQ ID NO:7:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:7:

GAAAAGATGG AATGTGACCG                                              20

(2) INFORMATION FOR SEQ ID NO:8:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:8:

ATCTGAAGCG TTCTTATATC                                                 20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:9:

TGCTCCATTT TCTCCGATCC                                                 20

(2) INFORMATION FOR SEQ ID NO:10:

(i) SEQUENCE CHARACTERISTICS:
        (A) LENGTH: 1068 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:10:

```
Met Pro Pro Arg Pro Ser Ser Gly Glu Leu Trp Gly Ile His Leu Met
 1               5                  10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Val Thr Ile Lys His Glu
        35                  40                  45

Leu Phe Arg Glu Ala Arg Lys Tyr Pro Leu His Gln Leu Leu Gln Asp
    50                  55                  60

Glu Thr Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Val Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
```

-continued

```
                245                 250                 255
Cys Asp Glu Tyr Phe Leu Glu Lys Tyr Pro Leu Ser Gln Tyr Lys Tyr
                260                 265                 270
Ile Arg Ser Cys Ile Met Leu Gly Arg Met Pro Asn Leu Met Leu Met
                275                 280                 285
Ala Lys Glu Ser Leu Tyr Ser Gln Leu Pro Ile Asp Ser Phe Thr Met
            290                 295                 300
Pro Ser Tyr Ser Arg Arg Ile Ser Thr Ala Thr Pro Tyr Met Asn Gly
305                 310                 315                 320
Glu Thr Ser Thr Lys Ser Leu Trp Val Ile Asn Ser Ala Leu Arg Ile
                325                 330                 335
Lys Ile Leu Cys Ala Thr Tyr Val Asn Val Asn Ile Arg Asp Ile Asp
                340                 345                 350
Lys Ile Tyr Val Arg Thr Gly Ile Tyr His Gly Gly Glu Pro Leu Cys
                355                 360                 365
Asp Asn Val Asn Thr Gln Arg Val Pro Cys Ser Asn Pro Arg Trp Asn
            370                 375                 380
Glu Trp Leu Asn Tyr Asp Ile Tyr Ile Pro Asp Leu Pro Arg Leu Ala
385                 390                 395                 400
Arg Leu Cys Leu Ser Ile Cys Ser Val Lys Gly Arg Lys Gly Ala Lys
                405                 410                 415
Glu Glu His Cys Pro Leu Ala Trp Gly Asn Ile Asn Leu Phe Asp Tyr
                420                 425                 430
Thr Asp Thr Leu Val Ser Gly Lys Met Ala Leu Asn Leu Trp Pro Val
            435                 440                 445
Pro His Gly Leu Glu Asp Leu Leu Asn Pro Ile Gly Val Thr Gly Ser
            450                 455                 460
Asn Pro Asn Lys Glu Thr Pro Cys Leu Glu Leu Glu Phe Asp Trp Phe
465                 470                 475                 480
Ser Ser Val Val Lys Phe Pro Asp Met Ser Val Ile Glu Glu His Ala
                485                 490                 495
Asn Trp Ser Val Ser Arg Glu Ala Gly Phe Ser Tyr Ser His Thr Gly
                500                 505                 510
Leu Ser Asn Arg Leu Ala Arg Asp Asn Glu Leu Arg Glu Asn Asp Lys
            515                 520                 525
Glu Gln Leu Arg Ala Leu Cys Thr Arg Asp Pro Leu Ser Glu Ile Thr
            530                 535                 540
Glu Gln Glu Lys Asp Phe Leu Trp Ser His Arg His Tyr Cys Val Thr
545                 550                 555                 560
Ile Pro Glu Ile Leu Pro Lys Leu Leu Leu Ser Val Lys Trp Asn Ser
                565                 570                 575
Arg Asp Glu Val Ala Gln Met Tyr Cys Leu Val Lys Asp Trp Pro Pro
            580                 585                 590
Ile Lys Pro Glu Gln Ala Met Glu Leu Leu Asp Cys Asn Tyr Pro Asp
            595                 600                 605
Pro Met Val Arg Ser Phe Ala Val Arg Cys Leu Glu Lys Tyr Leu Thr
        610                 615                 620
Asp Asp Lys Leu Ser Gln Tyr Leu Ile Gln Leu Val Gln Val Leu Lys
625                 630                 635                 640
Tyr Glu Gln Tyr Leu Asp Asn Leu Leu Val Arg Phe Leu Leu Lys Lys
                645                 650                 655
Ala Leu Thr Asn Gln Arg Ile Gly His Phe Phe Phe Trp His Leu Lys
            660                 665                 670
```

-continued

```
Ser Glu Met His Asn Lys Thr Val Ser Gln Arg Phe Gly Leu Leu Leu
            675                 680                 685

Glu Ser Tyr Cys Arg Ala Cys Gly Met Tyr Leu Lys His Leu Asn Arg
        690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Gln Pro Asp Phe Met Asp Ala Leu Gln Gly Phe Leu
            740                 745                 750

Ser Pro Leu Asn Pro Ala His Gln Leu Gly Asn Leu Arg Leu Glu Glu
        755                 760                 765

Cys Arg Ile Met Ser Ser Ala Lys Arg Pro Leu Trp Leu Asn Trp Glu
    770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Tyr Thr Lys Thr Arg Glu
                965                 970                 975

Phe Glu Arg Phe Gln Glu Met Cys Tyr Lys Ala Tyr Leu Ala Ile Arg
            980                 985                 990

Gln His Ala Asn Leu Phe Ile Asn Leu Phe Ser Met Met Leu Gly Ser
        995                 1000                1005

Gly Met Pro Glu Leu Gln Ser Phe Asp Asp Ile Ala Tyr Ile Arg Lys
    1010                1015                1020

Thr Leu Ala Leu Asp Lys Thr Glu Gln Glu Ala Leu Glu Tyr Phe Thr
025                 1030                1035                1040

Lys Gln Met Asn Asp Ala His His Gly Gly Trp Thr Thr Lys Met Asp
                1045                1050                1055

Trp Ile Phe His Thr Ile Lys Gln His Ala Leu Asn
            1060                1065
```

(2) INFORMATION FOR SEQ ID NO:11:

(i) SEQUENCE CHARACTERISTICS:
    (A) LENGTH: 1070 amino acids
    (B) TYPE: amino acid
    (C) STRANDEDNESS: unknown
    (D) TOPOLOGY: linear (ii) MOLECULE TYPE: protein (xi) SEQUENCE DESCRIPTION: SEQ ID NO:11:

```
Met Cys Phe Ser Phe Ile Met Pro Pro Ala Met Ala Asp Ile Leu Asp
 1               5                  10                  15

Ile Trp Ala Val Asp Ser Gln Ile Ala Ser Asp Gly Ser Ile Pro Val
                20                  25                  30

Asp Phe Leu Leu Pro Thr Gly Ile Tyr Ile Gln Leu Glu Val Pro Arg
            35                  40                  45

Glu Ala Thr Ile Ser Tyr Ile Lys Gln Met Leu Trp Lys Gln Val His
        50                  55                  60

Asn Tyr Pro Met Phe Asn Leu Leu Met Asp Ile Asp Ser Tyr Met Phe
65                  70                  75                  80

Ala Cys Val Asn Gln Thr Ala Val Tyr Glu Glu Leu Glu Asp Glu Thr
                85                  90                  95

Arg Arg Leu Cys Asp Val Arg Pro Phe Leu Pro Val Leu Lys Leu Val
            100                 105                 110

Thr Arg Ser Cys Asp Pro Gly Glu Lys Leu Asp Ser Lys Ile Gly Val
        115                 120                 125

Leu Ile Gly Lys Gly Leu His Glu Phe Asp Ser Leu Lys Asp Pro Glu
    130                 135                 140

Val Asn Glu Phe Arg Arg Lys Met Arg Lys Phe Ser Glu Glu Lys Ile
145                 150                 155                 160

Leu Ser Leu Val Gly Leu Ser Trp Met Asp Trp Leu Lys Gln Thr Tyr
                165                 170                 175

Pro Pro Glu His Glu Pro Ser Ile Pro Glu Asn Leu Glu Asp Lys Leu
            180                 185                 190

Tyr Gly Gly Lys Leu Ile Val Ala Val His Phe Glu Asn Cys Gln Asp
        195                 200                 205

Val Phe Ser Phe Gln Val Ser Pro Asn Met Asn Pro Ile Lys Val Asn
    210                 215                 220

Glu Leu Ala Ile Gln Lys Arg Leu Thr Ile His Gly Lys Glu Asp Glu
225                 230                 235                 240

Val Ser Pro Tyr Asp Tyr Val Leu Gln Val Ser Gly Arg Val Glu Tyr
                245                 250                 255

Val Phe Gly Asp His Pro Leu Ile Gln Phe Gln Tyr Ile Arg Asn Cys
            260                 265                 270

Val Met Asn Arg Ala Leu Pro His Phe Ile Leu Val Glu Cys Cys Lys
        275                 280                 285

Ile Lys Lys Met Tyr Glu Gln Glu Met Ile Ala Ile Glu Ala Ala Ile
    290                 295                 300

Asn Arg Asn Ser Ser Asn Leu Pro Leu Pro Leu Pro Lys Lys Thr
305                 310                 315                 320

Arg Ile Ile Ser His Val Trp Glu Asn Asn Pro Phe Gln Ile Val
                325                 330                 335

Leu Val Lys Gly Asn Lys Leu Asn Thr Glu Glu Thr Val Lys Val His
            340                 345                 350

Val Arg Ala Gly Leu Phe His Gly Thr Glu Leu Leu Cys Lys Thr Ile
        355                 360                 365
```

-continued

```
Val Ser Ser Glu Val Ser Gly Lys Asn Asp His Ile Trp Asn Glu Pro
    370             375                 380
Leu Glu Phe Asp Ile Asn Ile Cys Asp Leu Pro Arg Met Ala Arg Leu
385                 390                 395                 400
Cys Phe Ala Val Tyr Ala Val Leu Asp Lys Val Lys Thr Lys Lys Ser
                405                 410                 415
Thr Lys Thr Ile Asn Pro Ser Lys Tyr Gln Thr Ile Arg Lys Ala Gly
            420                 425                 430
Lys Val His Tyr Pro Val Ala Trp Val Asn Thr Met Val Phe Asp Phe
        435                 440                 445
Lys Gly Gln Leu Arg Thr Gly Asp Ile Ile Leu His Ser Trp Ser Ser
    450                 455                 460
Phe Pro Asp Glu Leu Glu Glu Met Leu Asn Pro Met Gly Thr Val Gln
465                 470                 475                 480
Thr Asn Pro Tyr Thr Glu Asn Ala Thr Ala Leu His Val Lys Phe Pro
                485                 490                 495
Glu Asn Lys Lys Gln Pro Tyr Tyr Pro Pro Phe Asp Lys Ile Ile
            500                 505                 510
Glu Lys Ala Ala Glu Ile Ala Ser Ser Asp Ser Ala Asn Val Ser Ser
        515                 520                 525
Arg Gly Gly Lys Lys Phe Leu Pro Val Leu Lys Glu Ile Leu Asp Arg
    530                 535                 540
Asp Pro Leu Ser Gln Leu Cys Glu Asn Glu Met Asp Leu Ile Trp Thr
545                 550                 555                 560
Leu Arg Gln Asp Cys Arg Glu Ile Phe Pro Gln Ser Leu Pro Lys Leu
                565                 570                 575
Leu Leu Ser Ile Lys Trp Asn Lys Leu Glu Asp Val Ala Gln Leu Gln
            580                 585                 590
Ala Leu Leu Gln Ile Trp Pro Lys Leu Pro Pro Arg Glu Ala Leu Glu
        595                 600                 605
Leu Leu Asp Phe Asn Tyr Pro Asp Gln Tyr Val Arg Glu Tyr Ala Val
    610                 615                 620
Gly Cys Leu Arg Gln Met Ser Asp Glu Glu Leu Ser Gln Tyr Leu Leu
625                 630                 635                 640
Gln Leu Val Gln Val Leu Lys Tyr Glu Pro Phe Leu Asp Cys Ala Leu
                645                 650                 655
Ser Arg Phe Leu Leu Glu Arg Ala Leu Gly Asn Arg Arg Ile Gly Gln
            660                 665                 670
Phe Leu Phe Trp His Leu Arg Ser Glu Val His Ile Pro Ala Val Ser
        675                 680                 685
Val Gln Phe Gly Val Ile Leu Glu Ala Tyr Cys Arg Gly Ser Val Gly
    690                 695                 700
His Met Lys Val Leu Ser Lys Gln Val Glu Ala Leu Asn Lys Leu Lys
705                 710                 715                 720
Thr Leu Asn Ser Leu Ile Lys Leu Asn Ala Val Lys Leu Asn Arg Ala
                725                 730                 735
Lys Gly Lys Glu Ala Met His Thr Cys Leu Lys Gln Ser Ala Tyr Arg
            740                 745                 750
Glu Ala Leu Ser Asp Leu Gln Ser Pro Leu Asn Pro Cys Val Ile Leu
        755                 760                 765
Ser Glu Leu Tyr Val Glu Lys Cys Lys Tyr Met Asp Ser Lys Met Lys
    770                 775                 780
Pro Leu Trp Leu Val Tyr Asn Asn Lys Val Phe Gly Glu Asp Ser Val
```

```
                785                 790                 795                 800
Gly Val Ile Phe Lys Asn Gly Asp Asp Leu Arg Gln Asp Met Leu Thr
                805                 810                 815
Leu Gln Met Leu Arg Leu Met Asp Leu Leu Trp Lys Glu Ala Gly Leu
                820                 825                 830
Asp Leu Arg Met Leu Pro Tyr Gly Cys Leu Ala Thr Gly Asp Arg Ser
                835                 840                 845
Gly Leu Ile Glu Val Val Ser Thr Ser Glu Thr Ile Ala Asp Ile Gln
            850                 855                 860
Leu Asn Ser Ser Asn Val Ala Ala Ala Ala Phe Asn Lys Asp Ala
865                 870                 875                 880
Leu Leu Asn Trp Leu Lys Glu Tyr Asn Ser Gly Asp Asp Leu Asp Arg
                885                 890                 895
Ala Ile Glu Glu Phe Thr Leu Ser Cys Ala Gly Tyr Cys Val Ala Ser
                900                 905                 910
Tyr Val Leu Gly Ile Gly Asp Arg His Ser Asp Asn Ile Met Val Lys
            915                 920                 925
Lys Thr Gly Gln Leu Phe His Ile Asp Phe Gly His Ile Leu Gly Asn
            930                 935                 940
Phe Lys Ser Lys Phe Gly Ile Lys Arg Glu Arg Val Pro Phe Ile Leu
945                 950                 955                 960
Thr Tyr Asp Phe Ile His Val Ile Gln Gln Gly Lys Thr Gly Asn Thr
                965                 970                 975
Glu Lys Phe Gly Arg Phe Arg Gln Cys Cys Glu Asp Ala Tyr Leu Ile
            980                 985                 990
Leu Arg Arg His Gly Asn Leu Phe Ile Thr Leu Phe Ala Leu Met Leu
            995                 1000                1005
Thr Ala Gly Leu Pro Glu Leu Thr Ser Val Lys Asp Ile Gln Tyr Leu
        1010                1015                1020
Lys Asp Ser Leu Ala Leu Gly Lys Ser Glu Glu Ala Leu Lys Gln
025                 1030                1035                1040
Phe Lys Gln Lys Phe Asp Glu Ala Leu Arg Glu Ser Trp Thr Thr Lys
                1045                1050                1055
Val Asn Trp Met Ala His Thr Val Arg Lys Asp Tyr Arg Ser
            1060                1065                1070

(2) INFORMATION FOR SEQ ID NO:12:

(i) SEQUENCE CHARACTERISTICS:
        (A) LENGTH: 1101 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:12:

Met Glu Leu Glu Asn Tyr Lys Gln Pro Val Val Leu Arg Glu Asp Asn
1               5                   10                  15
Cys Arg Arg Arg Arg Met Lys Pro Arg Ser Ala Ala Ser Leu Ser
            20                  25                  30
Ser Met Glu Leu Ile Pro Ile Glu Phe Val Leu Pro Thr Ser Gln Arg
            35                  40                  45
Lys Cys Lys Ser Pro Glu Thr Ala Leu Leu His Val Ala Gly His Gly
        50                  55                  60
Asn Val Glu Gln Met Lys Ala Gln Val Trp Leu Arg Ala Leu Glu Thr
```

```
              65                  70                  75                  80
Ser Val Ala Ala Asp Phe Tyr His Arg Leu Gly Pro His His Phe Leu
                    85                  90                  95
Leu Leu Tyr Gln Lys Lys Gly Gln Trp Tyr Glu Ile Tyr Asp Lys Tyr
                   100                 105                 110
Gln Val Val Gln Thr Leu Asp Cys Leu Arg Tyr Trp Lys Ala Thr His
                   115                 120                 125
Arg Ser Pro Gly Gln Ile His Leu Val Gln Arg His Pro Pro Ser Glu
                   130                 135                 140
Glu Ser Gln Ala Phe Gln Arg Gln Leu Thr Ala Leu Ile Gly Tyr Asp
145                150                 155                 160
Val Thr Asp Val Ser Asn Val His Asp Glu Leu Glu Phe Thr Arg
                   165                 170                 175
Arg Gly Leu Val Thr Pro Arg Met Ala Glu Val Ala Ser Arg Asp Pro
                   180                 185                 190
Lys Leu Tyr Ala Met His Pro Trp Val Thr Ser Lys Pro Leu Pro Glu
                   195                 200                 205
Tyr Leu Trp Lys Lys Ile Ala Asn Asn Cys Ile Phe Ile Val Ile His
                   210                 215                 220
Arg Ser Thr Thr Ser Gln Thr Ile Lys Val Ser Pro Asp Asp Thr Pro
225                230                 235                 240
Gly Ala Ile Leu Gln Ser Phe Phe Thr Lys Met Ala Lys Lys Lys Ser
                   245                 250                 255
Leu Met Asp Ile Pro Glu Ser Gln Ser Glu Gln Asp Phe Val Leu Arg
                   260                 265                 270
Val Cys Gly Arg Asp Glu Tyr Leu Val Gly Glu Thr Pro Ile Lys Asn
                   275                 280                 285
Phe Gln Trp Val Arg His Cys Leu Lys Asn Gly Glu Glu Ile His Val
                   290                 295                 300
Val Leu Asp Thr Pro Pro Asp Pro Ala Leu Asp Glu Val Arg Lys Glu
305                310                 315                 320
Glu Trp Pro Leu Val Asp Asp Cys Thr Gly Val Thr Gly Tyr His Glu
                   325                 330                 335
Gln Leu Thr Ile His Gly Lys Asp His Glu Ser Val Phe Thr Val Ser
                   340                 345                 350
Leu Trp Asp Cys Asp Arg Lys Phe Arg Val Lys Ile Arg Gly Ile Asp
                   355                 360                 365
Ile Pro Val Leu Pro Arg Asn Thr Asp Leu Thr Val Phe Val Glu Ala
                   370                 375                 380
Asn Ile Gln His Gly Gln Gln Val Leu Cys Gln Arg Arg Thr Ser Pro
385                390                 395                 400
Lys Pro Phe Thr Glu Glu Val Leu Trp Asn Val Trp Leu Glu Phe Ser
                   405                 410                 415
Ile Lys Ile Lys Asp Leu Pro Lys Gly Ala Leu Leu Asn Leu Gln Ile
                   420                 425                 430
Tyr Cys Gly Lys Ala Pro Ala Leu Ser Ser Lys Ala Ser Ala Glu Ser
                   435                 440                 445
Pro Ser Ser Glu Ser Lys Gly Lys Val Arg Leu Leu Tyr Tyr Val Asn
                   450                 455                 460
Leu Leu Leu Ile Asp His Arg Phe Leu Leu Arg Arg Gly Glu Tyr Val
465                470                 475                 480
Leu His Met Trp Gln Ile Ser Gly Lys Gly Glu Asp Gln Gly Ser Phe
                   485                 490                 495
```

```
Asn Ala Asp Lys Leu Thr Ser Ala Thr Asn Pro Asp Lys Glu Asn Ser
            500                 505                 510
Met Ser Ile Ser Ile Leu Leu Asp Asn Tyr Cys His Pro Ile Ala Leu
            515                 520                 525
Pro Lys His Gln Pro Thr Pro Asp Pro Glu Gly Asp Arg Val Arg Ala
            530                 535                 540
Glu Met Pro Asn Gln Leu Arg Lys Gln Leu Glu Ala Ile Ile Ala Thr
545                 550                 555                 560
Asp Pro Leu Asn Pro Leu Thr Ala Glu Asp Lys Glu Leu Leu Trp His
                565                 570                 575
Phe Arg Tyr Glu Ser Leu Lys His Pro Lys Ala Tyr Pro Lys Leu Phe
            580                 585                 590
Ser Ser Val Lys Trp Gly Gln Gln Glu Ile Val Ala Lys Thr Tyr Gln
            595                 600                 605
Leu Leu Ala Arg Arg Glu Val Trp Asp Gln Ser Ala Leu Asp Val Gly
            610                 615                 620
Leu Thr Met Gln Leu Leu Asp Cys Asn Phe Ser Asp Glu Asn Val Arg
625                 630                 635                 640
Ala Ile Ala Val Gln Lys Leu Glu Ser Leu Glu Asp Asp Asp Val Leu
                645                 650                 655
His Tyr Leu Leu Gln Leu Val Gln Ala Val Lys Phe Glu Pro Tyr His
            660                 665                 670
Asp Ser Ala Leu Ala Arg Phe Leu Leu Lys Arg Gly Leu Arg Asn Lys
            675                 680                 685
Arg Ile Gly His Phe Leu Phe Trp Phe Leu Arg Ser Glu Ile Ala Gln
            690                 695                 700
Ser Arg His Tyr Gln Gln Arg Phe Ala Val Ile Leu Glu Ala Tyr Leu
705                 710                 715                 720
Arg Gly Cys Gly Thr Ala Met Leu His Asp Phe Thr Gln Gln Val Gln
                725                 730                 735
Val Ile Glu Met Leu Gln Lys Val Thr Leu Asp Ile Lys Ser Leu Ser
                740                 745                 750
Ala Glu Lys Tyr Asp Val Ser Ser Gln Val Ile Ser Gln Leu Lys Gln
            755                 760                 765
Lys Leu Glu Asn Leu Gln Asn Ser Gln Leu Pro Glu Ser Phe Arg Val
            770                 775                 780
Pro Tyr Asp Pro Gly Leu Lys Ala Gly Ala Leu Ala Ile Glu Lys Cys
785                 790                 795                 800
Lys Val Met Ala Ser Lys Lys Pro Leu Trp Leu Glu Phe Lys Cys
                805                 810                 815
Ala Asp Pro Thr Ala Leu Ser Asn Glu Thr Ile Gly Ile Ile Phe Lys
            820                 825                 830
His Gly Asp Asp Leu Arg Gln Asp Met Leu Ile Leu Gln Ile Leu Arg
            835                 840                 845
Ile Met Glu Ser Ile Trp Glu Thr Glu Ser Leu Asp Leu Cys Leu Leu
850                 855                 860
Pro Tyr Gly Cys Ile Ser Thr Gly Asp Lys Ile Gly Met Ile Glu Ile
865                 870                 875                 880
Val Lys Asp Ala Thr Thr Ile Ala Lys Ile Gln Gln Ser Thr Val Gly
                885                 890                 895
Asn Thr Gly Ala Phe Lys Asp Glu Val Leu Asn His Trp Leu Lys Glu
            900                 905                 910
```

```
Lys Ser Pro Thr Glu Glu Lys Phe Gln Ala Ala Val Glu Arg Phe Val
        915                 920                 925

Tyr Ser Cys Ala Gly Tyr Cys Val Ala Thr Phe Val Leu Gly Ile Gly
        930                 935             940

Asp Arg His Asn Asp Asn Ile Met Ile Thr Glu Thr Gly Asn Leu Phe
945                 950                 955                 960

His Ile Asp Phe Gly His Ile Leu Gly Asn Tyr Lys Ser Phe Leu Gly
                965                 970                 975

Ile Asn Lys Glu Arg Val Pro Phe Val Leu Thr Pro Asp Phe Leu Phe
        980                 985                 990

Val Met Gly Thr Ser Gly Lys Lys Thr Ser Pro His Phe Gln Lys Phe
        995                 1000                1005

Gln Asp Ile Cys Val Lys Ala Tyr Leu Ala Leu Arg His His Thr Asn
    1010                1015                1020

Leu Leu Ile Ile Leu Phe Ser Met Met Leu Met Thr Gly Met Pro Gln
025                 1030                1035                1040

Leu Thr Ser Lys Glu Asp Ile Glu Tyr Ile Arg Asp Ala Leu Thr Val
                1045                1050                1055

Gly Lys Asn Glu Glu Asp Ala Lys Lys Tyr Phe Leu Asp Gln Ile Glu
                1060                1065                1070

Val Cys Arg Asp Lys Gly Trp Thr Val Gln Phe Asn Trp Phe Leu His
        1075                1080                1085

Leu Val Leu Gly Ile Lys Gln Gly Glu Lys His Ser Ala
        1090                1095                1100
```

(2) INFORMATION FOR SEQ ID NO:13:

(i) SEQUENCE CHARACTERISTICS:
        (A) LENGTH: 13 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:13:

```
Ile Phe Lys Asn Gly Asp Asp Leu Arg Gln Asp Met Leu
1               5                   10
```

(2) INFORMATION FOR SEQ ID NO:14:

(i) SEQUENCE CHARACTERISTICS:
        (A) LENGTH: 6 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:14:

```
His Ile Asp Phe Gly His
1               5
```